United States Patent [19]
Doi et al.

[11] Patent Number: 5,343,390
[45] Date of Patent: Aug. 30, 1994

[54] METHOD AND SYSTEM FOR AUTOMATED SELECTION OF REGIONS OF INTEREST AND DETECTION OF SEPTAL LINES IN DIGITAL CHEST RADIOGRAPHS

[75] Inventors: Kunio Doi, Willowbrook; Xuan Chen; Shigehiko Katsuragawa, both of Chicago, all of Ill.

[73] Assignee: Arch Development Corporation, Chicago, Ill.

[21] Appl. No.: 843,721

[22] Filed: Feb. 28, 1992

[51] Int. Cl.$^5$ .............. G06F 15/00; G06F 15/42; H04N 5/30; H04N 1/40
[52] U.S. Cl. ................ 364/413.16; 364/413.13; 364/413.22; 378/901; 378/98.2; 382/6; 382/22
[58] Field of Search ............. 358/111; 364/413.13, 364/413.16, 413.22, 413.23; 378/99, 901; 382/6, 22, 52, 54

[56] References Cited

U.S. PATENT DOCUMENTS

| | | | |
|---|---|---|---|
| 4,538,179 | 8/1985 | Tsutomu et al. | 358/166 |
| 4,804,842 | 2/1989 | Nakajima | 250/327.2 |
| 4,839,807 | 6/1989 | Doi et al. | 364/413.13 |
| 4,851,984 | 7/1989 | Doi et al. | 364/413.23 |
| 4,875,165 | 10/1989 | Fencil et al. | 364/413.22 |
| 4,907,156 | 3/1990 | Doi et al. | 364/413.13 |
| 4,918,534 | 4/1990 | Lam et al. | 225/358 |
| 5,072,384 | 12/1991 | Doi et al. | 364/413.13 |

OTHER PUBLICATIONS

MacMahon et al, "Effect of Digital Unsharp Masking on the Detectability of Interstitial Infiltrates and Pneumothoraces" *Proceedings of SPIE*, 1985; pp. 246-252; Dialog #02089824 (File 8).
Gonzalez; *Digital Image Processing;* 1987; Addison-Wesley Publishing Company; pp. 331-367.
Ballard et al; *Computer Vision;* 1982; Prentice-Hall; pp. 70-88.
Chen et al; "Automated Selection of Regions of Interest for Quantitative Analysis of Lung Textures in Digital Chest Radiographs"; *Med. Phys.* 1993, 20/4 (975-982); Dialog #8946136 (File 73).
Lams et al. "Spatial Resolution Requirements for Digital Chest Radiographs"; *Radiology;* vol. 158, No. 1 pp. 11-19; Jan. 1986; Dialog #02684653 (File 2).
Sanada et al; "Image Feature Analysis and Computer-aided Diagnosis in Digital Radiography"; *Am. Assoc. Phys. Med.;* Sep./Oct. 1992.
Powell et al; "Localization of Inter-rib Spaces for Lung Texture Analysis and Computer-aided Diagnosis in Digital Chest Images"; Med. Phys. 1988, 15/4 (581-587); Dialog #07204393 (File 72).

*Primary Examiner*—Roy N. Envall, Jr.
*Assistant Examiner*—Stephen R. Tkacs
*Attorney, Agent, or Firm*—Oblon, Spivak, McClelland, Maier & Neustadt

[57] ABSTRACT

An automated method and system for discriminating between normal lungs and abnormal lungs having interstitial disease and/or septal lines, wherein a large number of adjacent regions of interest (ROIs) are selected, corresponding to an area on a digital image of a patient's lungs. The ROIs each contain a number of square or rectangular pixel arrays and are selected to sequentially fill in the total selected area of the lungs to be analyzed. A background trend is removed from each individual ROI and the ROIs are then analyzed to determine those exhibiting sharp edges, i.e., high edge gradients. A percentage of these sharp-edged ROIs are removed from the original sample based on the edge gradient analysis, a majority of which correspond to rib-edge containing ROIs. After removal of the sharp-edged ROIs, texture measurements are taken on the remaining sample in order to compare such data with predetermined data for normal and abnormal lungs. Thus, a computerized scheme for quantitative analysis of interstitial lung diseases and/or septal lines appearing in digitized chest radiographs can be implemented in practical clinical situations.

42 Claims, 25 Drawing Sheets

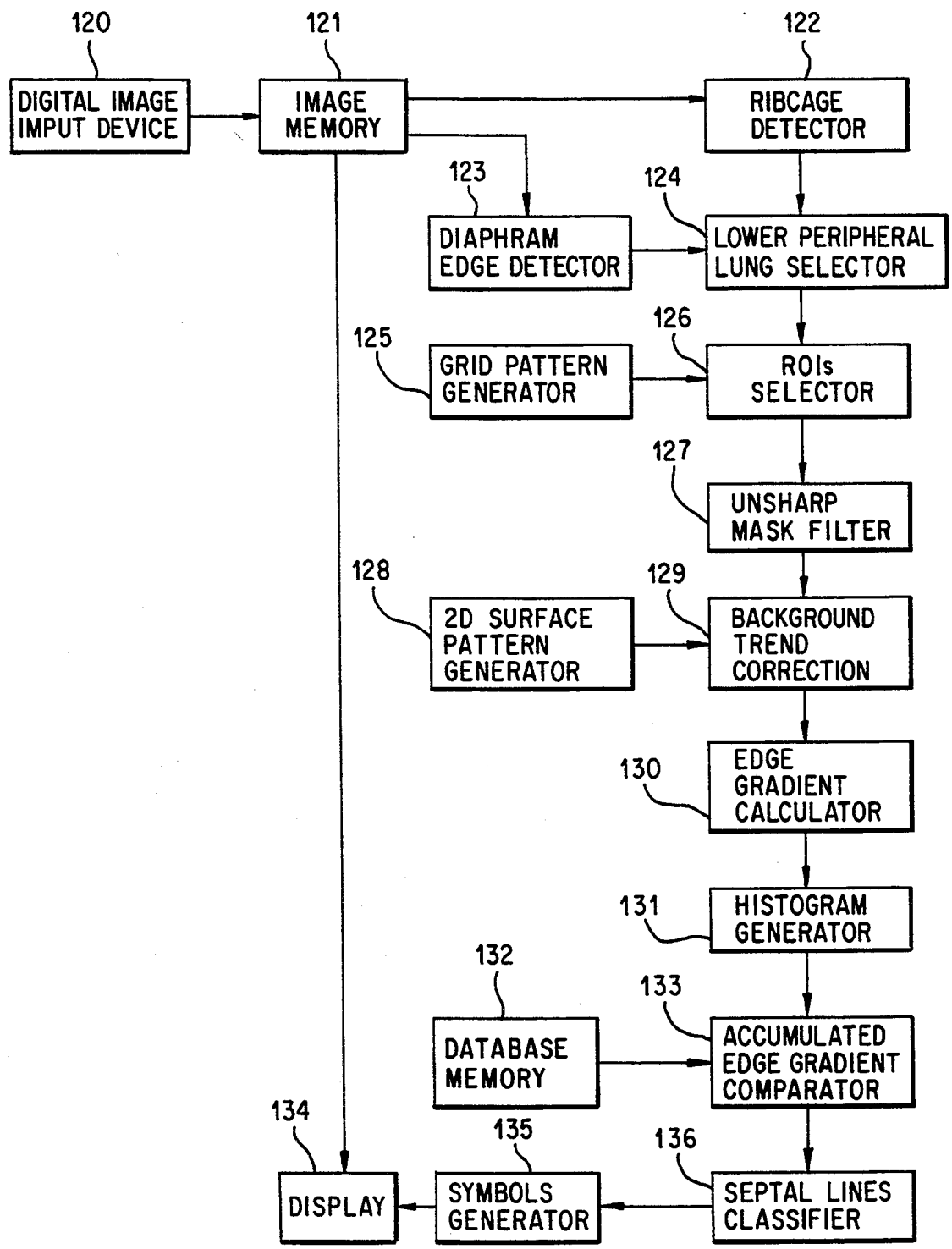
F I G. 15B

METHOD AND SYSTEM FOR AUTOMATED SELECTION OF REGIONS OF INTEREST AND DETECTION OF SEPTAL LINES IN DIGITAL CHEST RADIOGRAPHS

The present invention was made in part with U.S. Government support under grant number 2 R01 CA24806-11 from the Department of Health and Human Services and the National Cancer Institute. The U.S. Government has certain rights in the invention.

BACKGROUND OF THE INVENTION

1. Field of the Invention

The invention relates to a method and apparatus for the implementation of a computerized scheme used in the quantitative analysis of interstitial lung diseases through the provision of a fully automated method and system where a large number of regions of interest (ROIs) covering large peripheral areas of the lungs are selected. A greater number of texture measures are taken in order to discriminate normal lungs from abnormal lungs having interstitial diseases.

2. Discussion of Background

Evaluation of interstitial disease from chest radiographs is one of the most difficult tasks for diagnostic radiologists. This difficulty is related to the numerous patterns and complex variations in the X-ray images, the lack of a firmly established correlation between radiologic and pathological findings, and the subjective terms used in the description of various patterns. In recent years, digital chest radiography has been implemented in a computerized scheme which has been shown to be capable of detecting with accuracy interstitial diseases of the lungs. The computerized method can detect potentially abnormal lung texture patterns on the basis of quantitative measurements of the severity of abnormalities, and the subjectivity involved in the evaluation can be reduced as the accuracy of radiologic interpretation is increased.

In order to detect and characterize interstitial disease, there has recently been developed a computerized scheme, based on Fourier analysis techniques, for quantifying lung textures in digital chest radiographs. Such a method is disclosed in U.S. Pat. No. 4,839,807 to Doi et al, incorporated herein by reference. In this method, a conventional posterior-anterior (PA) chest radiograph is digitized with a Fuji drum scanner system employing a 0.1 mm pixel size and a 10-bit gray scale. Approximately 20 square regions of interest (ROIs) with a $64 \times 64$ matrix size are selected from the intercostal spaces. Manually interactive operations are needed in the ROI selection for the avoidance of ribs. A non-uniform background trend caused by the gross anatomy of the lung and chest wall is corrected by fitting a two-dimensional surface to the original image in an ROI and subtraction of the fitted surface from the original image. Such a surface-fitting technique facilitates the determination of fluctuating patterns of the underlying lung texture for subsequent analysis and processing by a computer.

The root mean square (RMS) variation, also referred to as R, and the first moment of the power spectrum, commonly referred to as M, are then determined, by use of the two-dimensional Fourier transform, as quantitative measures of the magnitude and coarseness (or fineness), respectively, of the lung texture. The two-dimensional Fourier transformed data are defined in terms of a function $T(u,v)$ where u and v are spatial frequencies in a Cartesian coordinate system. The function $T(u,v)$ is band-pass filtered by another function known in the art as the human visual response $V(u,v)$ as a means of suppressing low frequency and high frequency components, in order to enhance differences between normal and abnormal lungs.

From the filtered data ($T(u,v)$, $V(u,v)$) the two texture measures R and M are obtained for each ROI. The ROIs are then classified as normal or abnormal on the basis of a comparison of these texture measures and a database derived from clinical cases. The database is obtained by determining average R and M values from lungs which were predetermined to be normal or abnormal. The normal lungs on average showed R values which were lower than those for the abnormal lungs and M values which were higher. The results are displayed on a CRT monitor, providing a "second opinion" as an aid to radiologists in their interpretation.

On the monitor, symbols that indicate the severity and pattern type of interstitial diseases are superimposed on a digitized version of the original radiograph. If an analyzed lung is determined to be abnormal based on the texture levels of R and M being higher or lower than threshold levels, each individual ROI having such abnormal R, M values is indicated on the monitor screen with either a circle (representing a nodular pattern), a square (representing a reticular pattern), or a hexagon (representing honeycomb or reticulo-nodular patterns). The magnitude or severity of the abnormal ROI is proportional to the size of the pattern on the screen. The estimated probability of normal (or abnormal) lungs for a given chest image is also provided based on the classification results of these ROIs and on their geometric locations in the lung. Such probability estimations are provided by receiver operating characteristic (ROC) curves which are curves representative of the relationship between the fraction of true-positive determinations of abnormal lungs, i.e., an abnormal diagnosis for an abnormal lung, and the fraction of false-positive determinations, i.e., an abnormal diagnosis for a normal lung. A comparison of ROC curves obtained by radiologists and by this computerized scheme suggests that the computerized approach can provide performance similar to that of human observers in distinguishing lungs with mild interstitial diseases from normal lungs. Thus, the computerized scheme can be used by radiologists as a means of checking their initial diagnoses. In this manner, false negatives may be reduced and the diagnostic accuracy improved by the use of this computer-aided scheme.

In the method discussed above, however, it is necessary to be able to select a large number of ROIs covering major peripheral portions of the lungs in order to provide a greater likelihood of detecting abnormal ROIs which may exist only in small, isolated regions of the lung. Thus, for implementation of the computerized scheme in practical clinical situations, it is required to select numerous adjacent ROIs of a digitized chest image and also to automate the selection process.

SUMMARY OF THE INVENTION

Accordingly, one object of the present invention is to provide a novel method and system for discriminating normal lungs which are free of interstitial disease from abnormal, diseased lungs.

A further object of the present invention is to provide a method and system for automated selection of a large number of ROIs covering large peripheral areas of each lung and for performing a computerized texture analysis on each ROI to determine M and R texture measures for each ROI.

Another object of the present invention is to eliminate the effects of ROI texture measurements for the ROIs which are located over ribs or other internal structures and artifacts other than the lungs.

A still further object is to provide an edge gradient analysis technique to the individual ROIs in order to detect those ROIs which exhibit edge gradient standard deviation values above a predetermined threshold value or in a selected upper percentage of all standard deviations calculated for all ROIs of the initial sample.

Another object is to provide an automated method for detecting septal lines in digital chest radiographs by using a similar technique of edge gradient analysis on a large number of automatically selected adjacent rectangular regions of interest (ROIs).

These and other objects are accomplished by providing a new, automated method and system for selecting a large number of adjacent ROIs covering a large peripheral portion of a lung image in a digitized chest radiograph. First, the peripheral lung regions are identified based on the automated detection of lung apices, ribcage and diaphragm edges. Then a large number of ROIs are selected sequentially by filling in of the identified peripheral regions. The number of ROIs is selected in order to nearly completely fill in the area of each identified peripheral region and thus cover a large portion of the patient's lungs. An edge gradient analysis is then performed in order to determine those ROIs with sharp edges, i.e., those which exhibit high edge gradients with standard deviation values above a predetermined threshold value or in a selected upper percentage of all calculated standard deviations. For this purpose, a gradient-weighted edge orientation histogram is employed. Approximately 200 to 400 ROIs which are automatically selected using this method will be used for lung texture analysis. Texture measures obtained for abnormal lungs using this automated ROI selection method and system showed significant differences from those for normal lungs.

As another important aspect of the present invention, the identification of septal lines in chest radiographs is performed, using an automated method employing similar concepts as the one discussed above, i.e., using the technique of gradient-orientation histogram analysis. In chest radiographs, septal lines are generally demonstrated as short linear opacities caused by enlargement of the interlobular septa. These lines are important hallmarks of pulmonary edema and other lung diseases. However, it is difficult to detect septal lines because of their small size and low contrast. The method and system of the present invention provide significant improvements in the detection and analysis of septal lines present in radiographic images.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 15B is a block diagram illustrating the overall system used to implement the method of automated detection of septal lines in digital chest radiographs;

DETAILED DESCRIPTION OF THE PREFERRED EMBODIMENTS

Figure 1A:
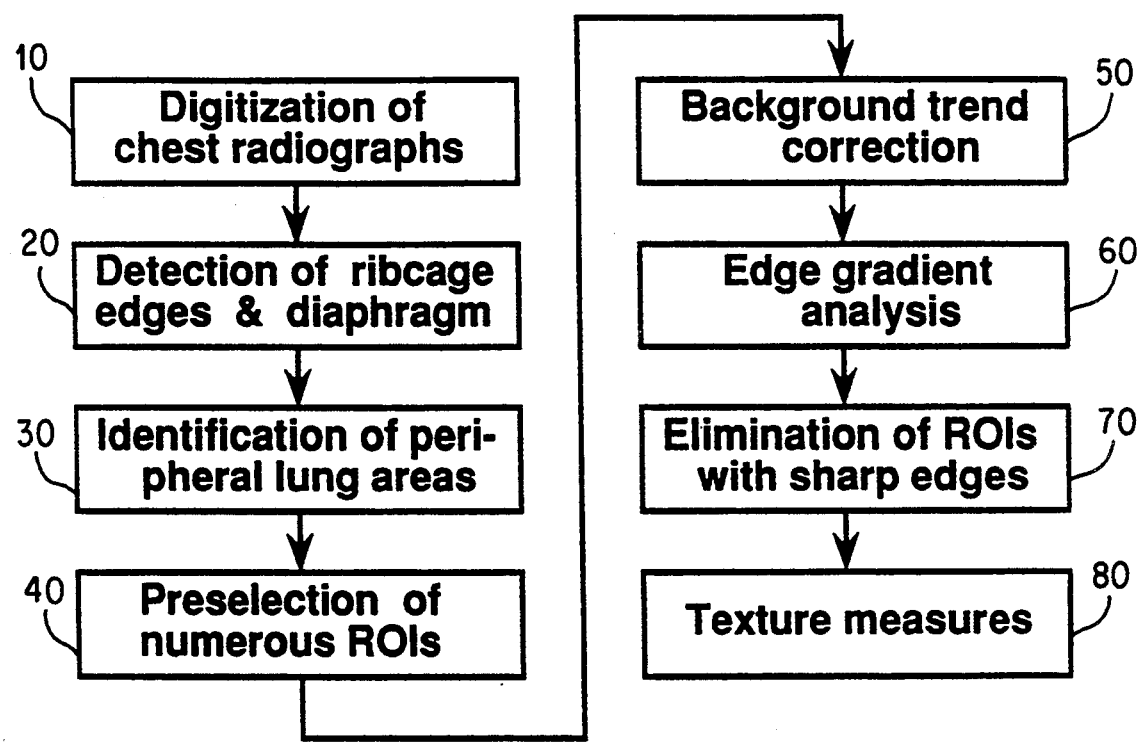
FIG. 1A is a flowchart illustrating the overall scheme for the automated selection method for selecting numerous ROIs and eliminating those ROIs with sharp edges prior to taking texture measurements of the remaining ROIs.

Referring now to the drawings, wherein like reference numerals designate identical or corresponding parts throughout the several views, and more particularly to FIG. 1 thereof, there is shown a flowchart for the overall scheme of the present invention, including the automated selection of ROIs covering large areas of the lungs, and for the elimination of ROIs with sharp edges. For fully automated selection of ROIs in large lung areas, the large peripheral lung areas are first identified based on automated detection of rib cage and diaphragm edges, and then numerous ROIs with $32 \times 32$ matrix size are selected in the form of a grid to fill in the identified area boundaries. Finally, the ROIs with sharp edges are removed by use of a gradient-weighted edge orientation histogram analysis. The overall scheme consists of (1) identification of peripheral lung areas, (2) initial selection of ROIs, (3) background trend correction, (4) edge gradient analysis based on gradient-weighted edge orientation histogram, and (5) removal of ROIs with sharp edges.

Interstitial disease tends to be more clearly visible in the peripheral lung regions than in the perihilar regions, because no large pulmonary vessels are present in the peripheral regions. Therefore, computerized analyses of lung textures in these regions are expected to be more accurate. The approximate shape and locations of peripheral lung regions can be identified based on the detection of lung apices, rib cage, and diaphragm edges which will be described in detail later. The apical regions are also avoided because it is difficult to select an ROI for texture analysis in the presence of the ribs and clavicles. A main concern of the present invention involves how the ribs affect the texture measures when the lung textures of numerous ROIs which cover large lung areas are analyzed, and how such an effect can be eliminated.

Figure 2:
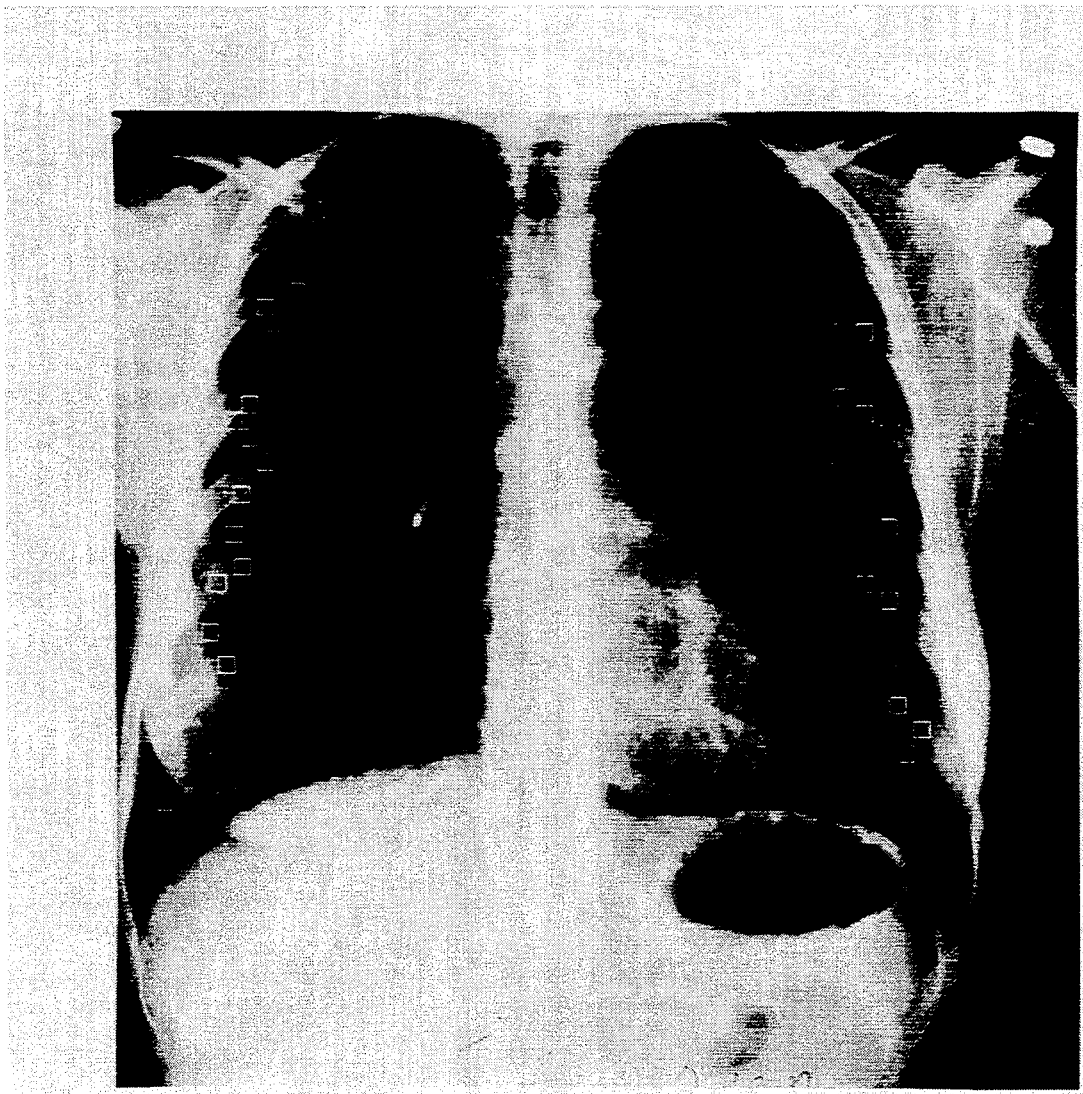
FIG. 2 is a normal chest image radiograph with ROIs marked by small white squares, which were selected manually from rib edges, areas over the ribs, and intercostal areas, in order to determine empirically, average data values for the RMS variation, and the first moment of power spectrum for the different regions.

In order to investigate this effect, manual selection of various ROIs from a normal chest image was performed on ROIs representing three groups according to their locations. The ROIs are selected from rib edges, areas over ribs and intercostal areas, as is illustrated in FIG. 2. Because a fast Fourier transform (FFT) algorithm is used for calculation of the texture measures, it is efficient to use matrix sizes of the ROI with powers of two, such as 16, 32, and 64. A $32 \times 32$ matrix size (5.6 mm $\times$ 5.6 mm) is used in a preferred embodiment, having a side length that is usually smaller than the width of space between two adjacent ribs.

Figure 3:
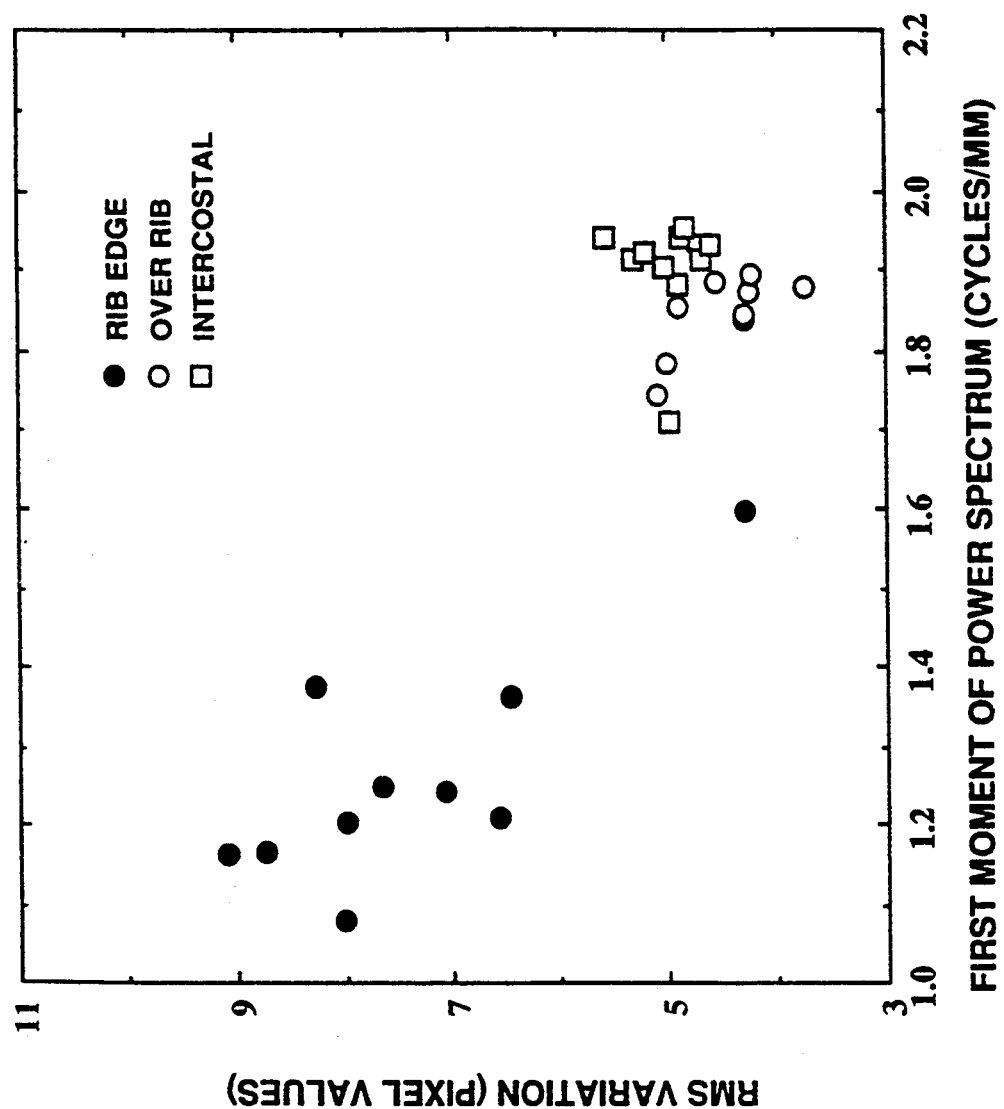
FIG. 3 is a graph illustrating the effect of ROI location on the RMS variation and first moment of the power spectrum, which are used for quantifying lung textures.

The RMS variation and the first moment of the power spectrum of the manually selected ROIs are calculated and plotted in FIG. 3. The ROIs with rib edges yield small first moments and large RMS variations, as abnormal lung textures tend to do. This result is attributable to the fact that a high-contrast rib edge has a large low-frequency content. However, the ROIs selected from over-rib areas indicate texture measures similar to those obtained from intercostal areas. Therefore, ROIs with rib edges must be eliminated for correct detection and characterization of interstitial disease, whereas the ROIs from over-rib areas can be included in lung texture analysis.

As shown in FIG. 3, the RMS variation is plotted along the vertical axis and the first moment of power spectrum is plotted along the horizontal axis. This graph indicates the relationship between R and M for the ROIs located in the three different regions. In particular, the rib-edge areas have high RMS variation values and low first moment of power spectrum values. The other two types of ROIs, over-rib ROIs and intercostal ROIs, have the opposite texture values, i.e., low RMS variation values with high first moment of power spectrum values.

The intercostal region ROIs are the regions with which the present invention is most concerned in analyzing. However, since the over-rib regions display very similar texture values as the intercostal ROIs, these over-rib ROIs can be included in the sampled data without a significant loss of determination accuracy. The rib-edge ROIs, on the other hand, must be eliminated in order to obtain true indications of abnormal lungs from normal lungs. This is because the ROIs over rib edges tend to display texture measurements of R and M which are similar to ROIs in an abnormal lung, i.e., high RMS variation values and low first moment of power spectrum values. In other words, the rib edge ROIs may give false-positive indications, identifying normal lungs as abnormal due to the high edge gradients that the rib-edge ROIs include.

Figure 4:
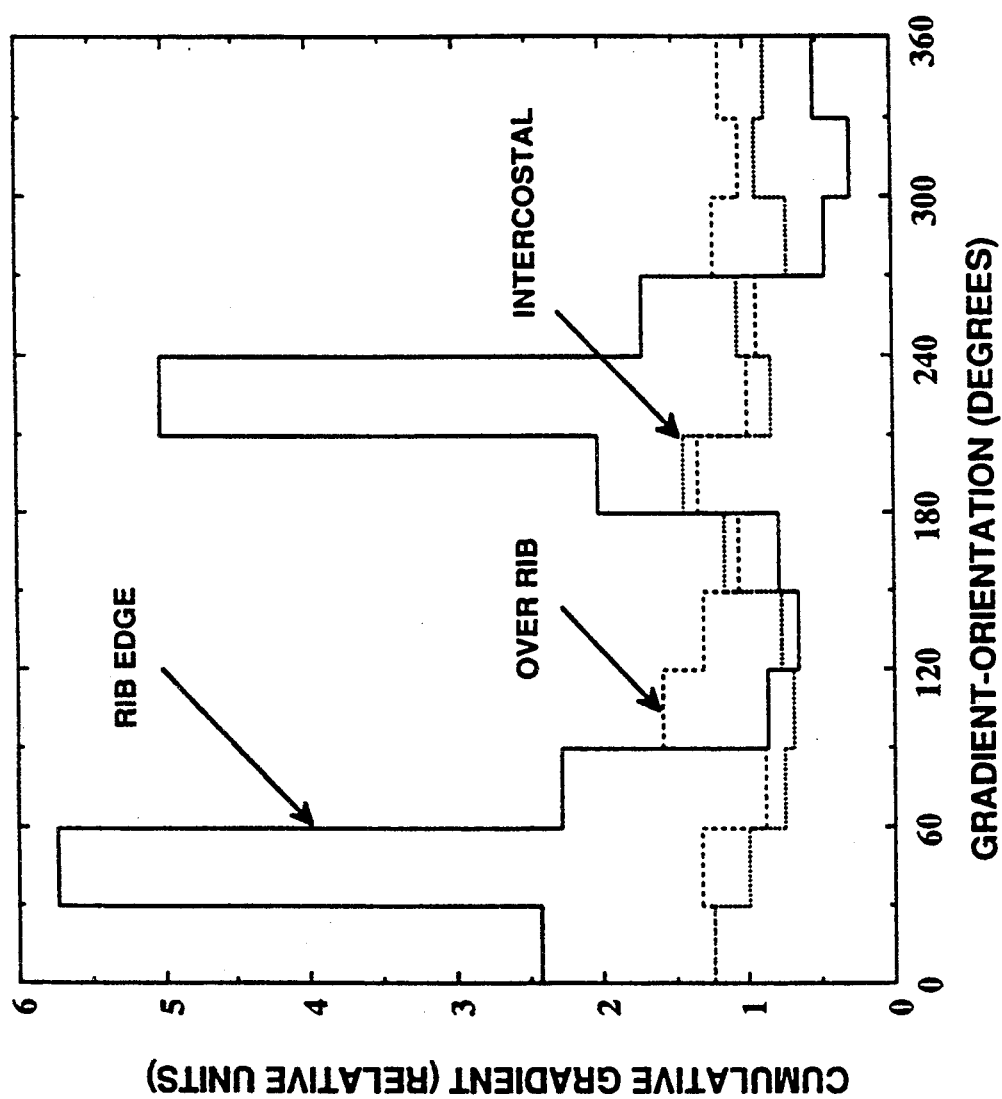
FIG. 4 is a graph illustrating the effect of ROI location on a gradient-weighted edge orientation histogram, with the three regions of rib edges, over-rib areas and intercostal regions shown.

As is indicated in FIG. 4, the over-rib and intercostal areas provide the ROIs over these areas with low cumulative gradient values throughout the full cycle of gradient orientation, i.e., from 0° to 360°. The rib edge regions, in contrast, display high gradient values at two points in the cycle, at approximately 30° and 210°. The overall standard deviations of the cumulative gradients for each of the three different locations for the ROIs are plotted in FIG. 5. The standard deviations for the over-rib and intercostal ROIs are seen to be low, ranging from 0.25 to 0.5 relative units. The rib edge ROIs, on the other hand, show standard deviations which are much higher. These range from 0.75 up to approximately 2.25 relative units. The fact that these standard deviations do not generally overlap, will allow the rib edge ROIs to be identified based on this criteria, and be removed before the final texture measure analysis is performed.

As shown in FIG. 2, the white border edges indicate the peripheral regions of the lungs and also the upper boundary edge of the diaphragm. The ROIs selected from these three regions, are analyzed so as to determine their edge gradient values and also their RMS variations, R, and their first moments of power spectrum values, M. These values are determined so as to provide a database of known values of edge gradient and texture measures for the rib edge, over-rib areas and the intercostal areas, all for a normal, disease-free lung.

FIG. 4 indicates the gradient-weighted orientation histograms of three ROIs selected from the rib-edge area, over-rib area, and intercostal area. It is clear that the variation of the histogram due to the large edge gradients in the ROI with rib edges is much larger than the variations of the other two ROIs.

Figure 5:
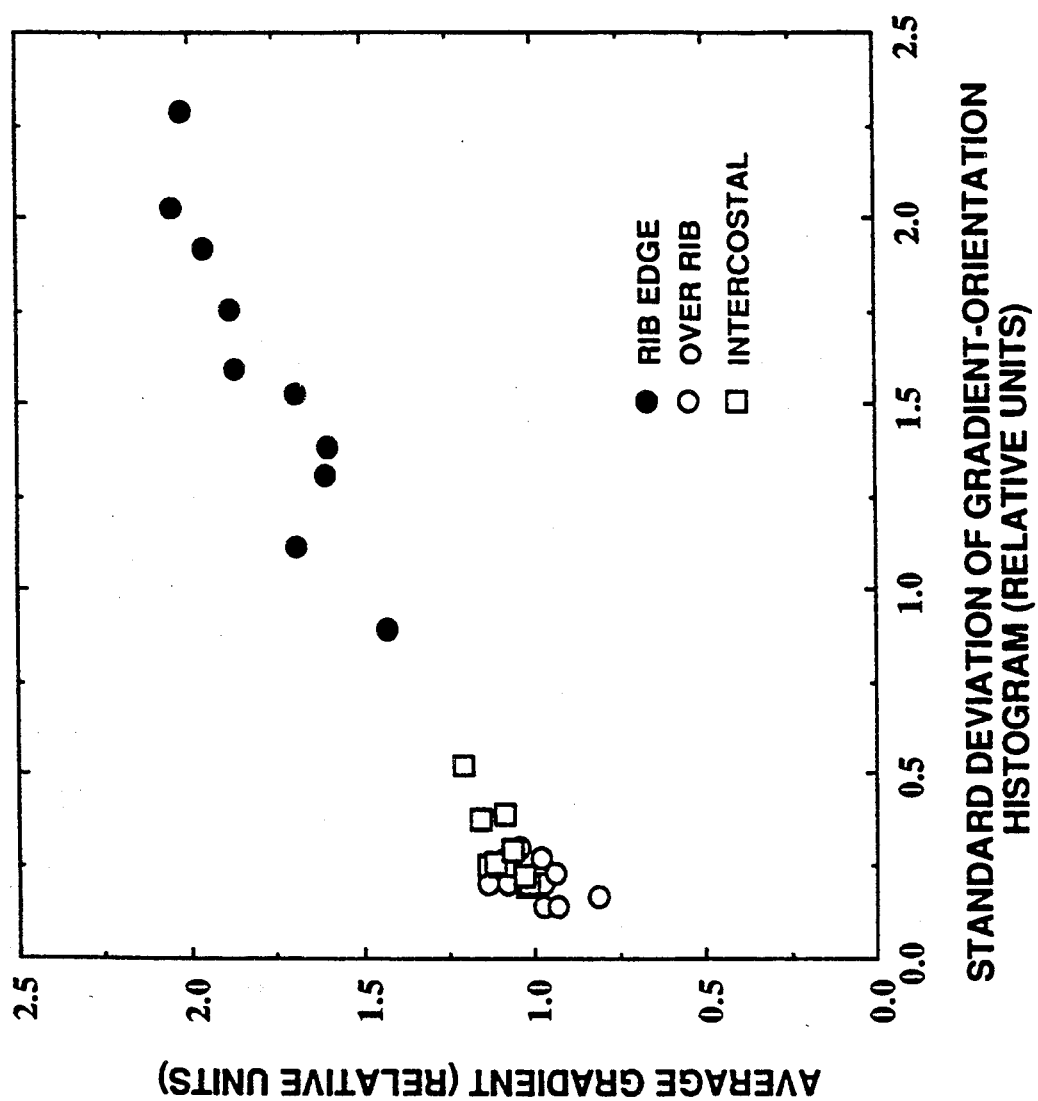
FIG. 5 is a graph of edge gradient analysis in terms of average and standard deviation of the gradient-weighted edge orientation histogram of FIG. 4.

FIG. 5 shows the averages and standard deviations of the histograms for manually selected ROIs. The standard deviation of the histogram indicates the magnitude of the variation of the histogram, and thus it is used as a measure for identifying the ROIs with sharp edges. It should be noted that the standard deviations for the ROIs with rib edges are much larger than those for other ROIs. This step also involves taking the standard deviations of the individual ROIs and plotting these values on a gradient orientation histogram, as illustrated in FIG. 4. Also, ROIs over other internal structures or artifacts, such as cardiac pacemakers, catheters, etc which may be present inside a patient's chest cavity, will also yield high standard deviations due to the appearance of sharp edges. Thus, in order to eliminate the possibility of false-positives due to these artifacts, such sharp-edged ROIs also need to be eliminated.

The analysis of a given patient's lungs in order to detect the presence of possible interstitial disease will now be described. As shown in FIG. 1A, in the first step (block 10), chest radiographs are digitized so as to provide a 2k×2k array of pixels used to cover a preselected area of the lung image. It has been found from previous studies that the difference between 0.1 and 0.2 mm pixel sizes for the detection and characterization of interstitial diseases in digital chest images is relatively insignificant. Therefore, a Konica laser scanner with a 0.175 mm pixel size and a 10-bit gray scale was used for the digitization of chest radiographs. The laser scanner is convenient for image digitization because of its speed. The small matrix image is useful for the reduction of computer processing time, which may be an important factor in clinical situations.

In the next step (block 20), a detection process is performed for detecting the rib cage edges and also the upper boundary of the diaphragm. Such a detection method is disclosed in U.S. Pat. No. 4,851,984, incorporated herein by reference.

Figure 6A:
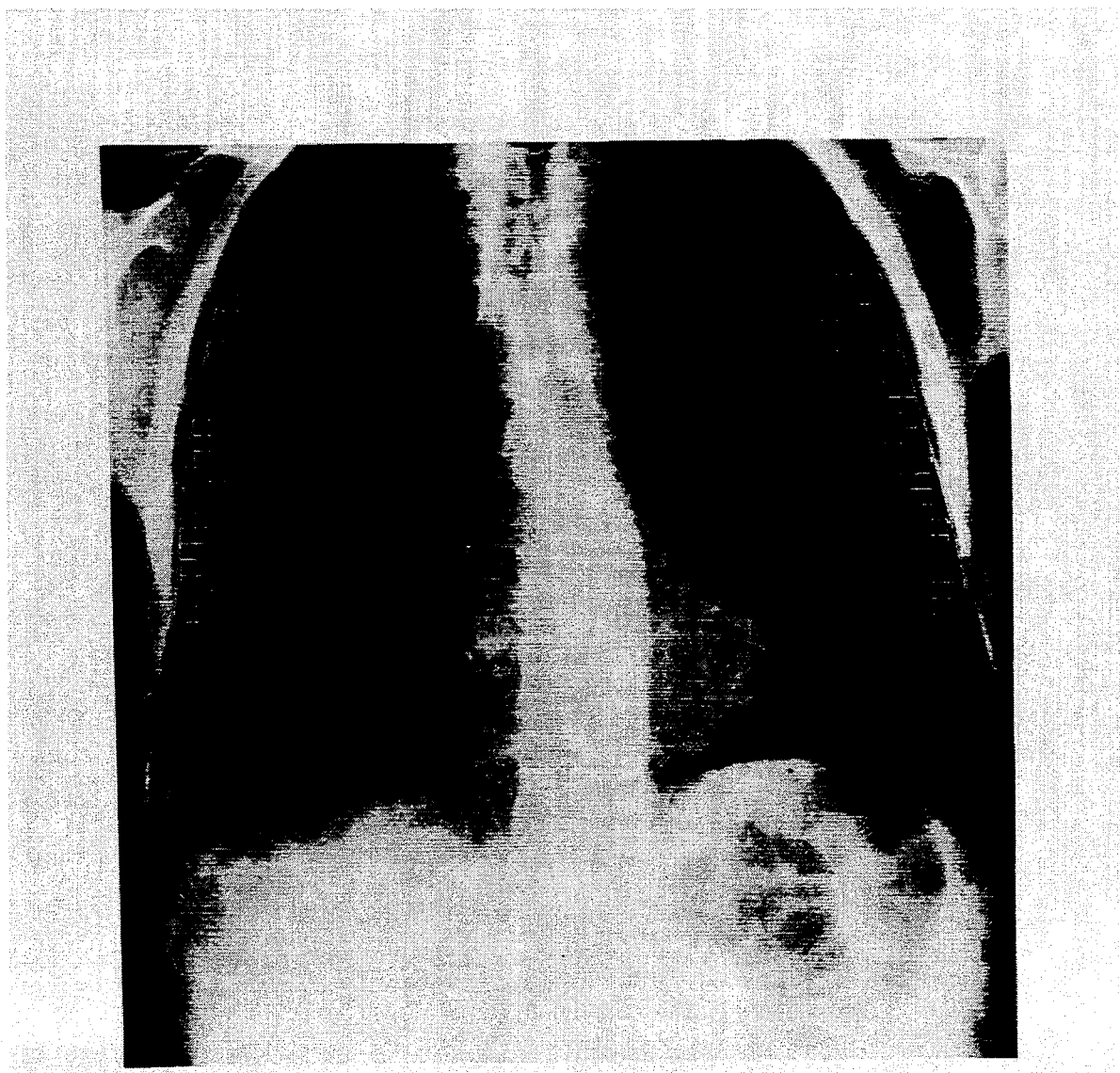
FIGS. 6A and 6B show peripheral lung regions indicated by the white contours, for abnormal and normal lung cases, respectively, and initially-selected ROIs marked by small white squares.
Figure 6B:

Once the outer boundaries of the rib cage edges and diaphragm are determined, the peripheral lung areas are identified in the next step (block 30) as follows. As shown in FIGS. 6A and 6B, the upper boundaries of the peripheral regions for both of the right and left lungs are determined at a distance below the lung apex equal to 20% of the lung height. The lower boundaries of the regions are determined at the top of the diaphragm. The outer boundaries are determined at 96% of the distance from the midline of the chest image to the rib cage edge. For determination of the inner boundaries, the percentage fraction is changed linearly from 50% at the upper boundary to 80% at the lower boundary. Thus, the width of the selected regions decreases toward the lower boundary to avoid overlap with relatively large pulmonary vessels which are commonly in the lower lungs. These fractions are determined empirically based on experimental data using different sized regions.

In the next step (block 40), numerous square (32×32 matrix) ROIs are selected by filling in of the identified peripheral lung regions fully and sequentially, as illustrated in FIGS. 6A and 6B. Edge gradient analysis is carried out for each ROI by calculation of the gradient-weighted edge orientation histogram. Next, the standard deviation of the histogram is obtained as a measure to be used in the removal of ROIs containing sharp edges. Those ROIs having edge gradient standard deviation values above a predetermined threshold value or in a selected upper percentage of all standard deviations are then removed.

After the preselection of the ROIs, a background trend correction step is performed (block 50). A background trend correction is needed because the trend due to the gross anatomy of the lung and chest wall can yield a large peak, like that of a step edge in the gradient-weighted edge orientation histogram, even if there is no rib edge in the ROI. The trend correction technique used in U.S. Pat. No. 4,851,984 is employed. In this step, the non-uniform background trend in each ROI is corrected by means of a two-dimensional surface fitting technique in order to determine the fluctuating patterns of the underlying lung texture.

Next, an edge gradient analysis is performed on each individual ROI (block 60), in order to determine those ROIs which have edge gradient values with standard deviations above a predetermined threshold value or in a selected upper percentage of all the standard deviations of the initial sample of ROIs. If a sharp edge is present in an ROI, the edge gradient in the direction perpendicular to this edge becomes very large, and thus this edge can be detected using the gradient-weighted edge orientation calculations described later. There are usually one or two peaks (approximately at a 180-degree interval) in the histogram, corresponding to a step-edge or a line-edge in the ROI, respectively. In a step-edge ROI there is only one density change, i.e. one sharp edge, whereas in a line-edge ROI there are two density changes due to a small "width" of the line passing through the ROI, thus yielding two sharp edges and two peaks in the histogram.

Based on the edge gradient analysis, the ROIs with sharp edges are determined and a variable number of these sharp-edged ROIs are eliminated from the sampled data based on high standard deviation gradient values (block 70), and will not be analyzed for texture measurements of the first moment of power spectrum, M, and the RMS variation, R (block 80). By elimination of these ROIs with sharp edges, the ROIs located over the rib edges are reduced. These rib edge ROIs tend to yield false positive determinations of abnormal lungs, due to their high R values and low M values, similar to ROIs with interstitial disease. The texture measure values of the individual ROIs will thus give a more accurate determination of abnormal lungs as abnormal and normal lungs as normal, due to the fact that the sharp-edged ROIs have been removed.

Figure 1B:
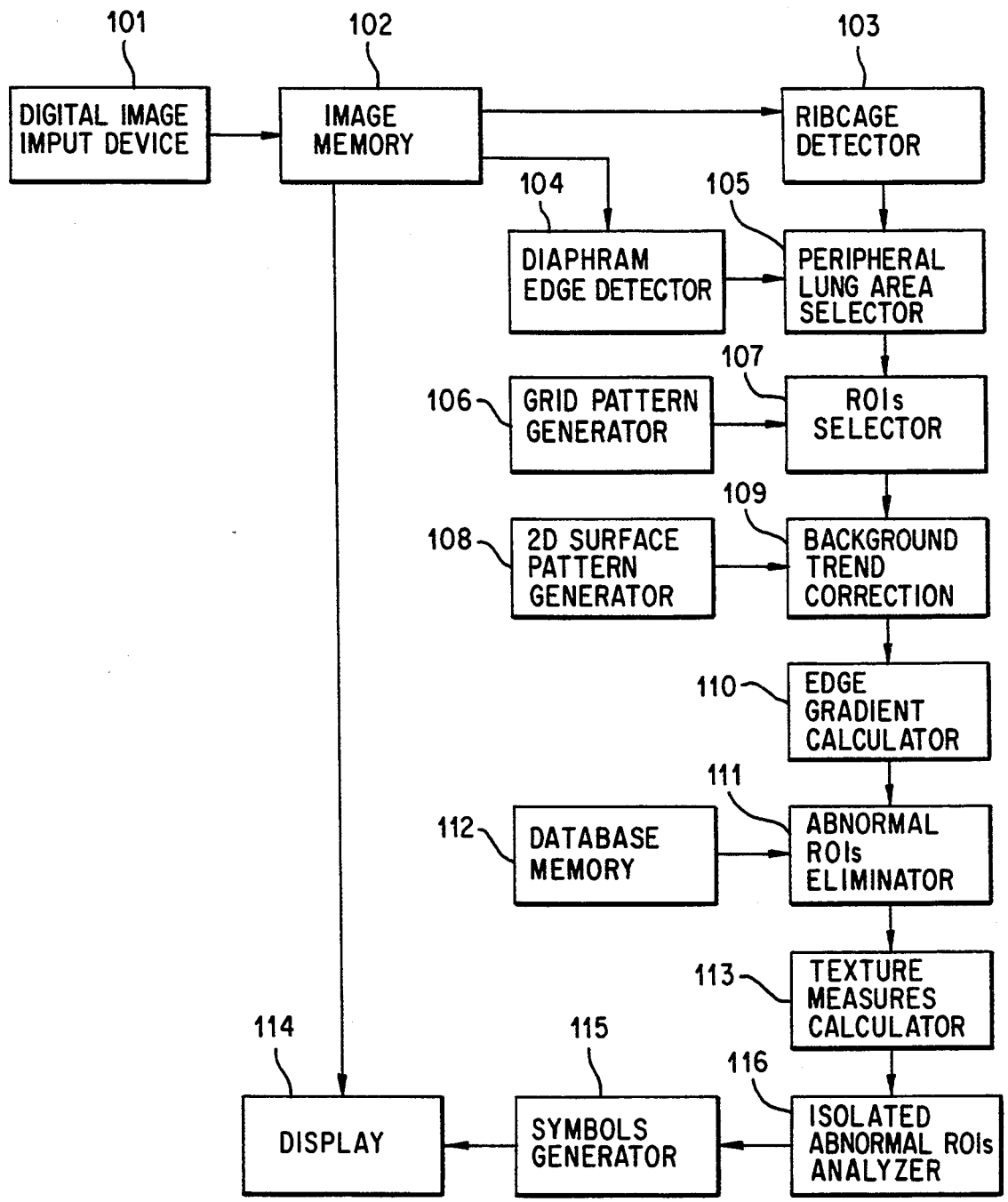
FIG. 1B is a block diagram illustration of the overall system used for implementing the method of automated selection of numerous ROIs and eliminating those ROIs with sharp edges prior to taking texture measurements of the remaining ROIs.

Referring now to FIG. 1B, there is shown the overall system used for the automated selection of numerous contiguous ROIs and the elimination of a portion of those ROIs having sharp edges. Initially, an object is input into digital input device 101 after the object has been digitized into a 2k×2k array of pixels and then is stored in image memory 102. The stored image is then output to ribcage detector 103 and diaphragm edge detector 104 where the boundaries of the lung regions are determined. The digitized object image is also output to display 114 where various symbols indicating information about the analyzed ROIs will be superimposed on the original digital image. After the ribcage and diaphragm boundaries have been identified, the peripheral regions of the lungs are next determined in the peripheral lung area selector 105. The output of the selector 105 and grid pattern generator 106 are then input into the ROIs selector 107 in order to fill in the identified peripheral lung areas on the digitized image.

Next, the ROIs are filtered through a background trend correction device 109 which receives input from two-dimensional surface pattern generator 108. After trend correction, an edge gradient calculator 110 generates edge gradient values for each ROI, and a standard deviation value is computed for each ROI. Those ROIs exhibiting standard deviation values above a predetermined threshold value or having a threshold value corresponding to a selected upper percentage of all calculated standard deviation values stored in database memory 112, are then eliminated by eliminator means 111. These eliminated ROIs will not undergo texture measurement analysis, but the remaining ROIs from the initial sample will have such measurements calculated in calculation device 113. As a "fine tuning" method of eliminating additional sharp edged ROIs, as will be described later, analyzer 116 is employed. Symbols generator 115 then generates various symbols which indicate the size, shape, severity, etc. of the ROIs that have undergone texture analysis, and these symbols are then superimposed on the original digitized X-ray image shown on display means 114.

The RMS variation, R, and the first moment of the power spectrum, M, are used as texture measures of the remaining ROIs, for quantifying lung textures, corresponding to the magnitude and coarseness of the texture, respectively. They are defined as follows:

$$R = \sqrt{\int_{-\infty}^{\infty} \int_{-\infty}^{\infty} V^2(u,v)|F(u,v)|^2 du dv} \tag{1}$$

and $$M = \frac{\int_{-\infty}^{\infty} \int_{-\infty}^{\infty} \sqrt{u^2 + v^2}\, V^2(u,v)|F(u,v)|^2 du dv}{\int_{-\infty}^{\infty} \int_{-\infty}^{\infty} V^2(u,v)|F(u,v)|^2 du dv} \tag{2}$$

where F(u,v) is the Fourier transform of texture patterns in an ROI after the background trend correction and V(u,v) is the visual system response where u and v are spatial frequencies, in a Cartesian coordinate system. The latter is used as a band-pass filter to suppress low-frequency components due to residual uncorrected background trends, and high frequency components due to, for example, radiographic mottle, in order to enhance the difference between normal and abnormal lung textures. It has been shown from previous studies that normal lung textures tend to have large M and small R, whereas abnormal lung textures yield small first moments and/or large RMS variations. Ribs in the chest image would have different texture measures because of the bone structure.

Edge gradients $G_x(m,n)$ in the horizontal direction and $G_y(m,n)$ in the vertical direction at a pixel location (m,n) are obtained by use of a Sobel operator:

$$G_x(m,n) = \{f(m+1,n-1)+2f(m+1,n)+f(m+1,n+1)\} - \{f(m-1,n-1)+2f(m-1,n)+f(m-1,n+1)\} \tag{3}$$

$$G_y(m,n) = \{f(m-1,n+1)+2f(m,n+1)+f(m+1,n+1)\} - \{f(m-1,n-1)+2f(m,n-1)+f(m+1,n-1)\} \tag{4}$$

where f(m,n) is the pixel value of the image at the location (m,n). The orientation of the edge gradient, $\theta(m,n)$ is given by $$\theta(m,n) = \tan^{(-1)}\left( \frac{G_y(m,n)}{G_x(m,n)} \right) \tag{5}$$

The amplitude of the edge gradient G(m,n) is given by $$G(m,n) = \sqrt{G_x^2(m,n) + G_y^2(m,n)}\,. \tag{6}$$

The gradient-orientation histogram, which indicates the angular distribution of the accumulated edge gradient within a given ROI, is determined by division of 360 degrees into 12 segments, so that the angle $\theta_k$ is defined as $$\theta_k = 30(k-1),\ k=1, 2, \ldots 12, \tag{7}$$

and the accumulated edge gradient $G(\theta_k)$ at the angle $\theta_k$ is given by $$G(\theta_k) = \sum_{m=1}^{M} \sum_{n=1}^{N} G(m,n),\ \theta_k - 15 \leq \theta \leq \theta_k + 15 \tag{8}$$

where M and N indicate the matrix size of the ROI.

For the display of calculated texture measures to be superimposed on a chest image, the method described in the U.S. Pat. No. 4,839,807 is employed which provides various sizes and shapes of markers representing the nature and the severity of the lung textures such as reticular, nodular and honeycomb patterns. The texture measures are normalized by using the average and the standard deviation of the corresponding texture measures obtained from a large number of normal cases in the database.

With this method, the texture pattern is considered normal when the normalized texture measures are below 2.0, namely, texture measures are less than two times the standard deviation for normal cases. When the texture measures are in the abnormal range, markers such as square, circle and hexagon for reticular, nodular and honeycomb patterns, respectively, are displayed by superimposing at positions where ROIs were located on the chest image. This method provides a very useful way to monitor the calculated texture measures in comparison with the actual texture patterns at many locations of the chest images.

It was found that by using this display method isolated "abnormal" ROIs are very likely to contain sharp edges. Therefore, these isolated "abnormal" ROIs are eliminated if all of the immediately adjacent ROIs do not contain abnormal texture measures. This "fine tuning" elimination of further sharp-edged ROIs which may be present due to rib edge ROIs, or ROIs over other internal structures or artifacts remarkably improves the distinction between normal and abnormal lungs.

Fifty normal cases and fifty abnormal cases with various interstitial diseases were studied. Approximately 300–600 ROIs with 32×32 matrix size were initially selected from the peripheral lung areas of each chest image. FIGS. 6A and 6B show the identified peripheral lung areas and the ROIs initially selected in a normal and an abnormal image, respectively. It will be that some ROIs contain apparent sharp rib edges. The standard deviations of the gradient-weighted edge orientation histograms were calculated for all of the initially selected ROIs.

As illustrated in FIGS. 6A and 6B, respectively, a normal pair of lungs and an abnormal pair of lungs are shown with the preselected grids of ROIs selected so as to cover a major portion of each lung. These ROIs are seen to cover the intercostal regions, the over-rib regions and also the rib edge regions. The rib edge ROIs are eliminated from the initial ROI sample in accordance with the technique of the present invention.

Figure 7:
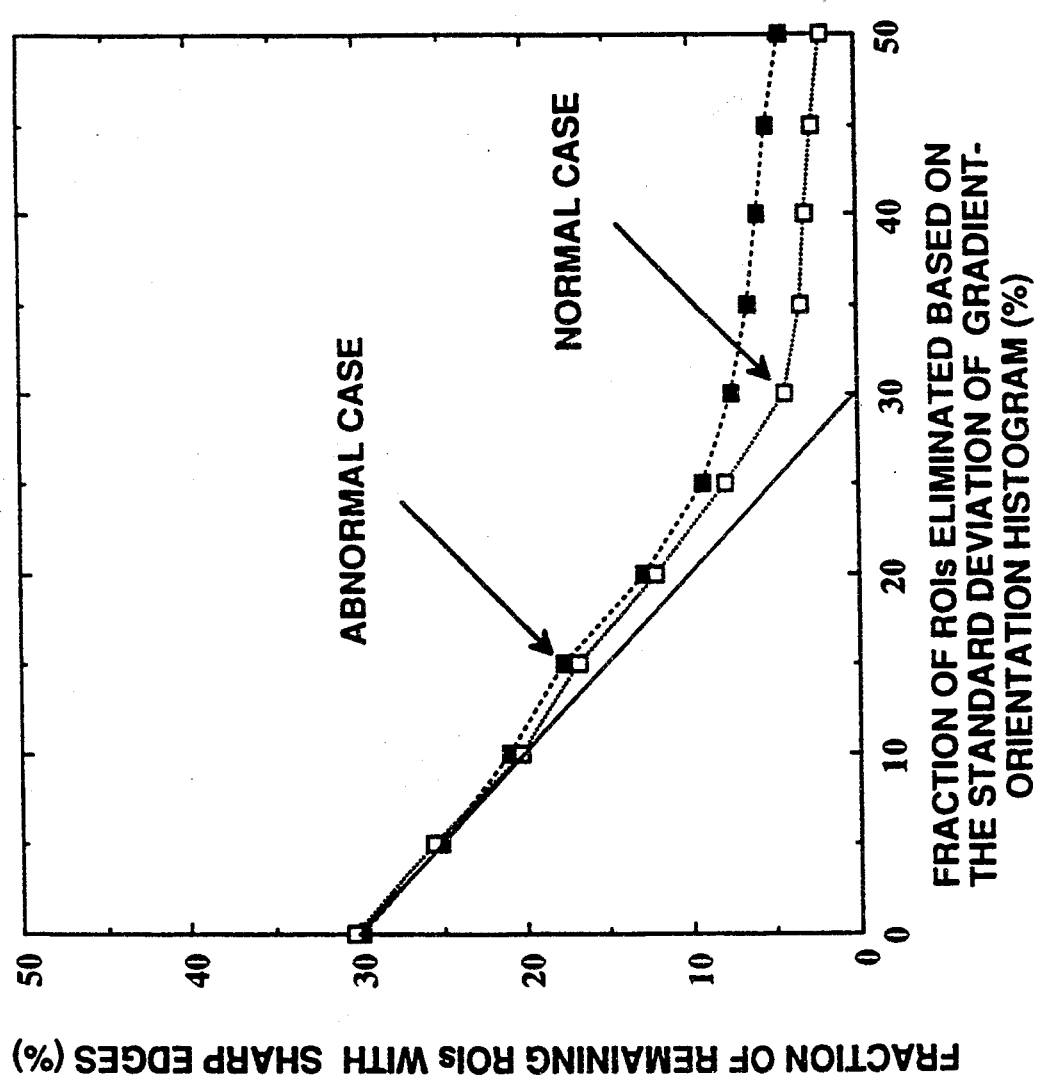
FIG. 7 shows an illustration of the effect of removal of ROIs with sharp edges for both abnormal and normal lung cases, and also the ideal case where all ROIs with sharp edges are removed.

FIG. 7 illustrates the relationship between the fraction of ROIs eliminated based on the standard deviation of gradient orientation histogram and the fraction of remaining ROIs with sharp edges. In a preferred embodiment, a 30% fraction of ROIs having sharp edges are eliminated, for reasons to be discussed later. The relationship between the remaining fraction of the ROIs with sharp edges and the fraction of the eliminated ROIs for both the normal and the abnormal cases is shown. Results for both normal and abnormal cases are very close to the ideal line at low eliminated fractions, and they gradually part at about 15%. This ideal line indicates a simple hypothetical case in which the large standard deviations should occur always due to the presence of sharp edges. The departure from this ideal line indicates that as the fraction of the eliminated ROIs increases, some ROIs which may not include sharp edges but contain relatively large texture components, would have been removed. It is believed that a loss of some ROIs due to this factor will not have a detrimental effect on the accuracy of texture analysis since the number of remaining ROIs is very large. The remaining fraction of ROIs with sharp edges in the abnormal image is slightly larger than that in the normal image, which seems to imply that the ROIs with abnormal lung textures tend to be removed in this process of eliminating ROIs with rib edges.

Figure 8:
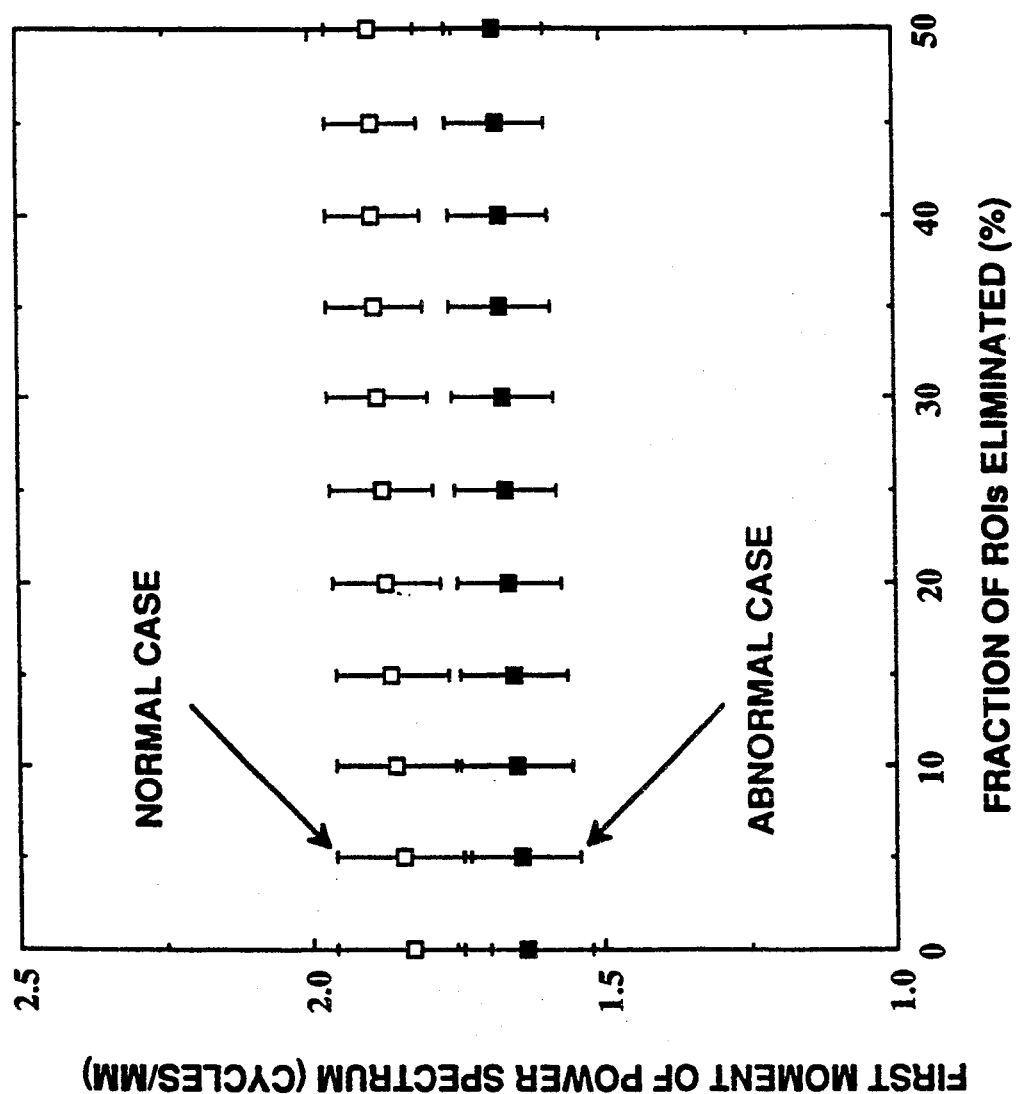
FIG. 8 illustrates the dependence of the first moment of power spectrum for remaining ROIs on the fraction of ROIs eliminated.
Figure 9:
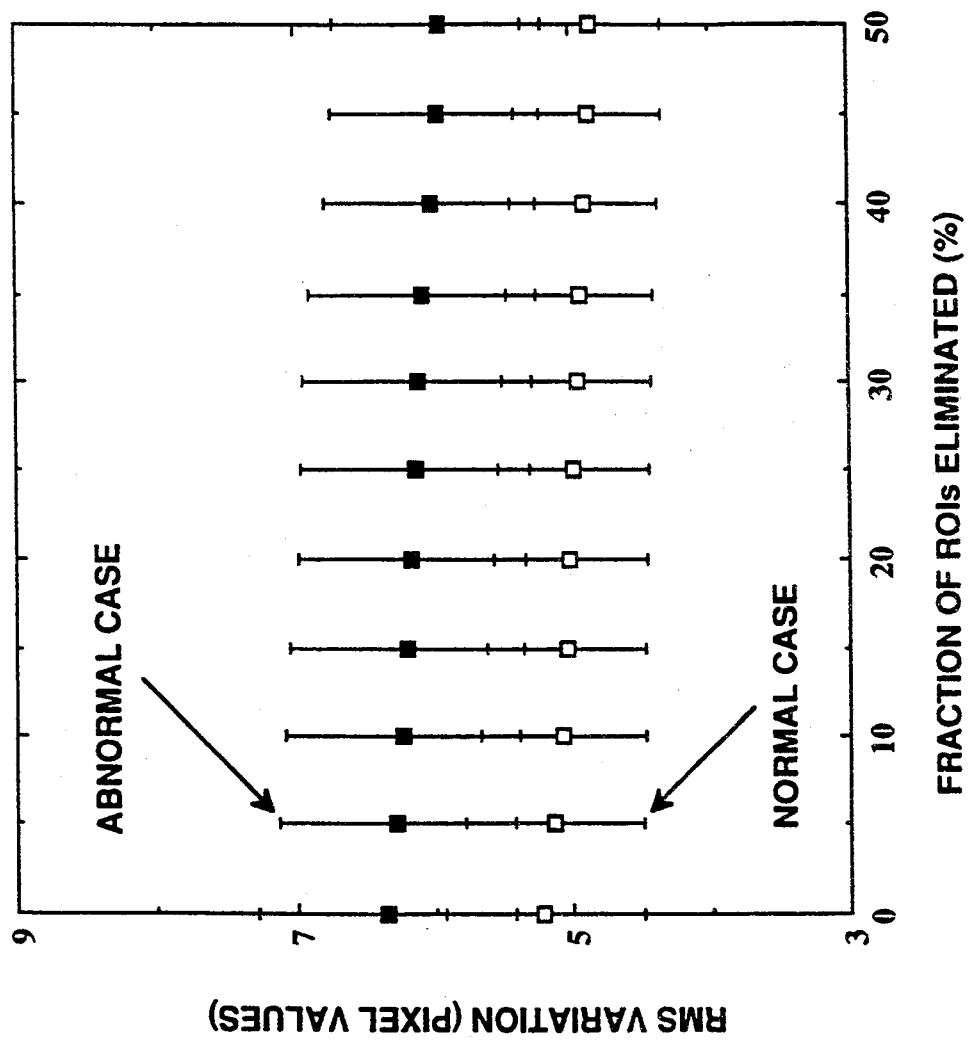
FIG. 9 shows the dependence of RMS variation for remaining ROIs on the fraction of ROIs eliminated.

FIGS. 8 and 9 graphically illustrate the relationship between the fraction of eliminated ROIs having sharp edges to the first moment of power spectrum, M, and the RMS variation, R, respectively. From these figures, it can be seen that as the fraction of ROIs eliminated increases, the differences between the R and M values becomes more significant. FIGS. 8 and 9 show the dependence of the first moment of the power spectrum and the dependence of the RMS variation, respectively, for the remaining ROIs, on the fraction of ROIs removed. Texture measures of normal and abnormal images tend to be separated more as the fraction of ROIs eliminated is increased.

Figure 10A:
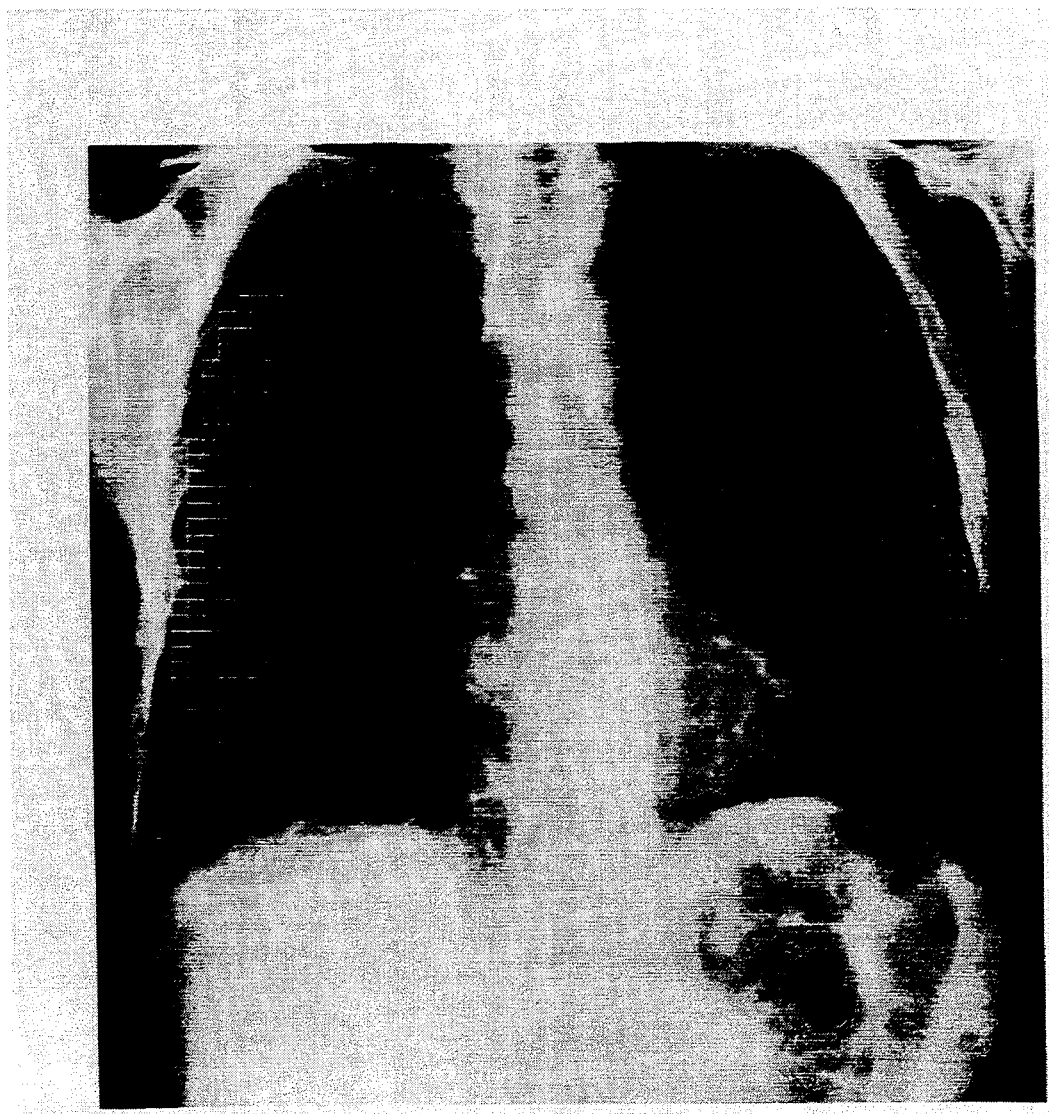
FIGS. 10A and 10B are, respectively, illustrations of chest radiographs showing the case where the ROIs are automatically selected by elimination of ROIs with sharp edges which are marked with white dots.
Figure 10B:
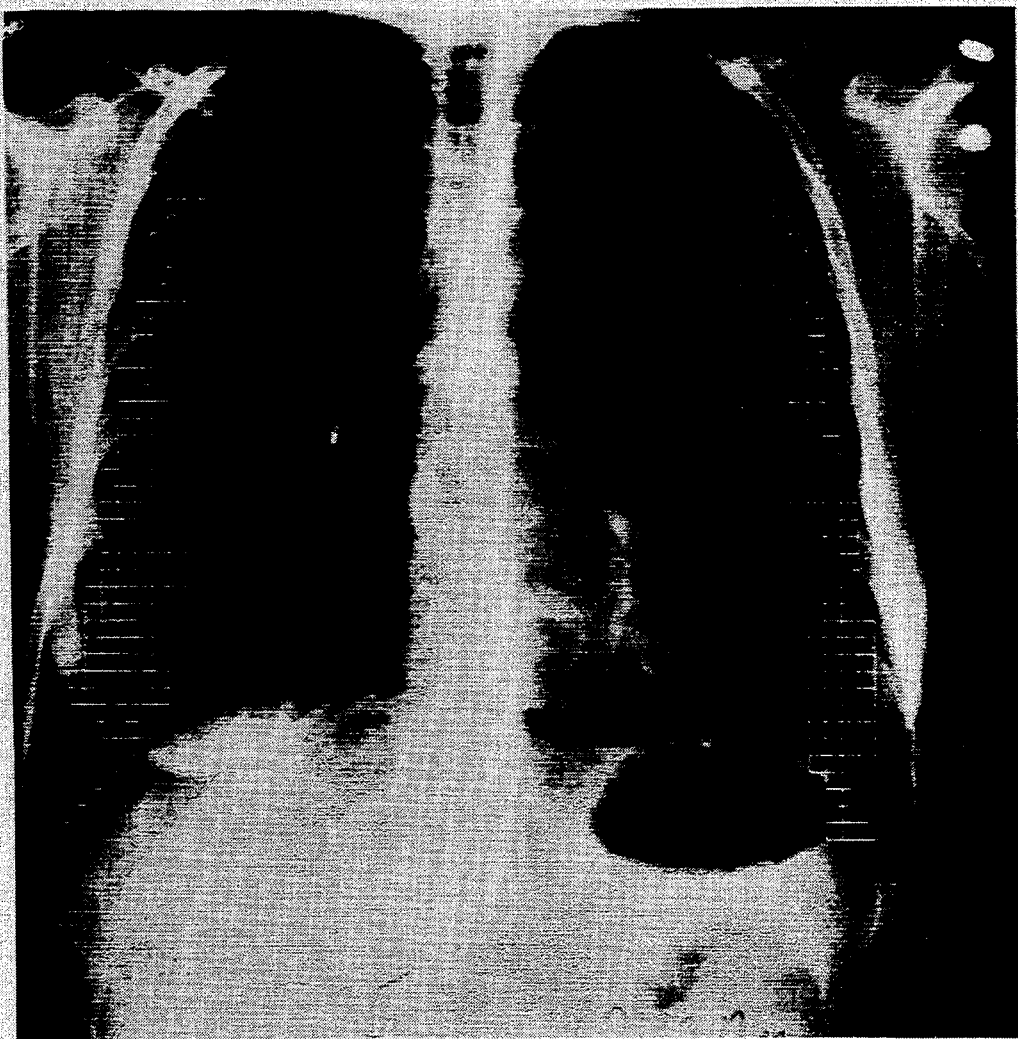

FIGS. 10A and 10B indicate the ROIs superimposed on the chest images after elimination of 30% of the initially selected ROIs (from FIG. 6A and 6B, respectively). The ROIs with white dots are those eliminated based on edge gradient analysis. Note that not only the ROIs with sharp rib edges, but also those with breast edges are removed. As can be seen from these figures, the eliminated ROIs are mainly those ROIs located over rib edges. These rib edge ROIs were determined by their high edge gradient values and corresponding high standard deviation values.

Figure 11:
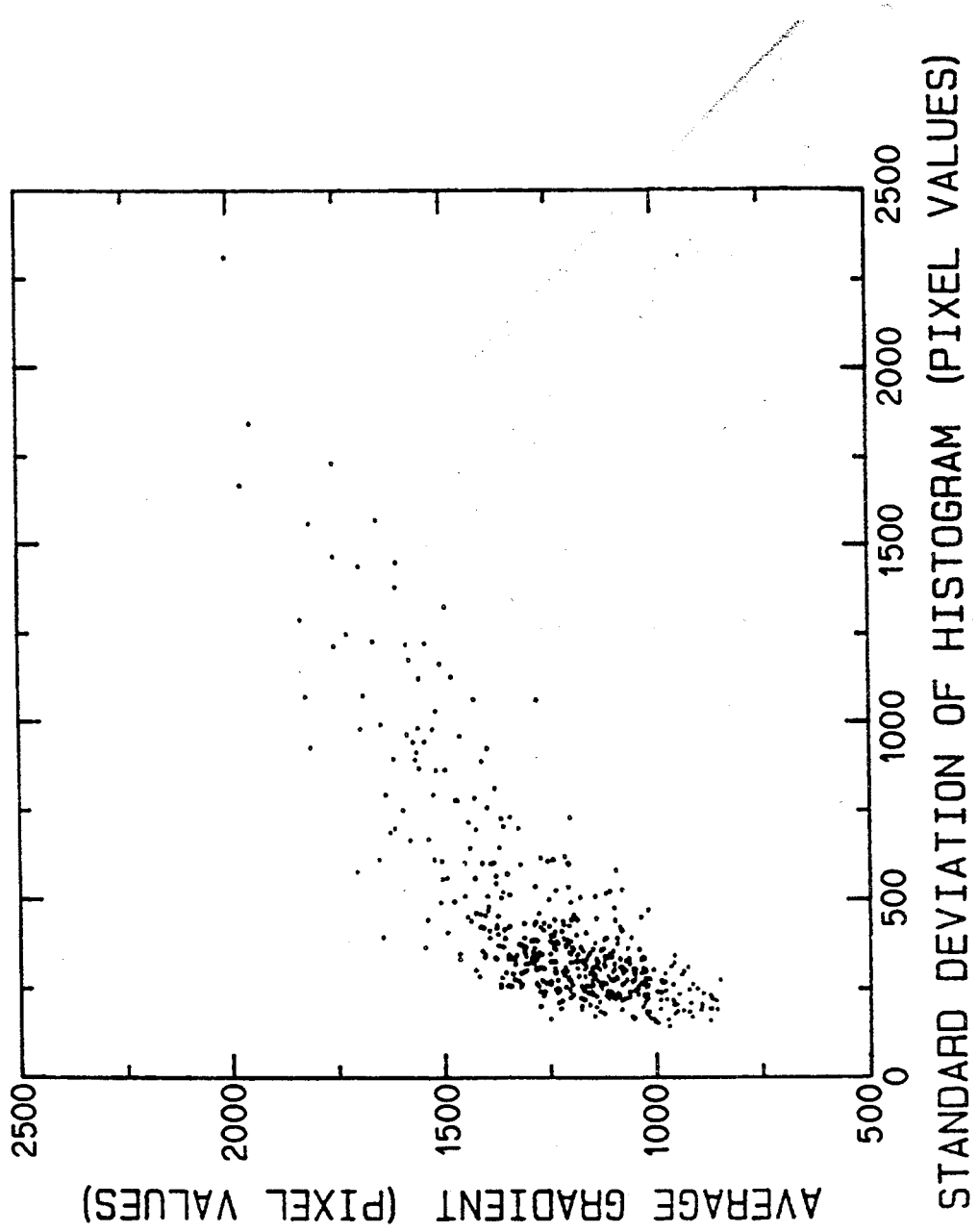
FIG. 11 shows the results of edge gradient analysis in terms of average and standard deviation of the gradient-weighted edge orientation histogram for the initially selected ROIs.

FIG. 11 shows the results of edge gradient analysis on the normal chest image in FIG. 6A. It is apparent that the standard deviation and average gradient are spread over a wide range. The results of edge gradient analysis in terms of the average and standard deviation of the gradient weighted edge orientation histogram for the initially selected ROIs are graphically illustrated. As is clear, a majority of the data values are clustered at the lower left-hand corner indicating a standard deviation of between 0 and 500 pixel values.

Figure 12:
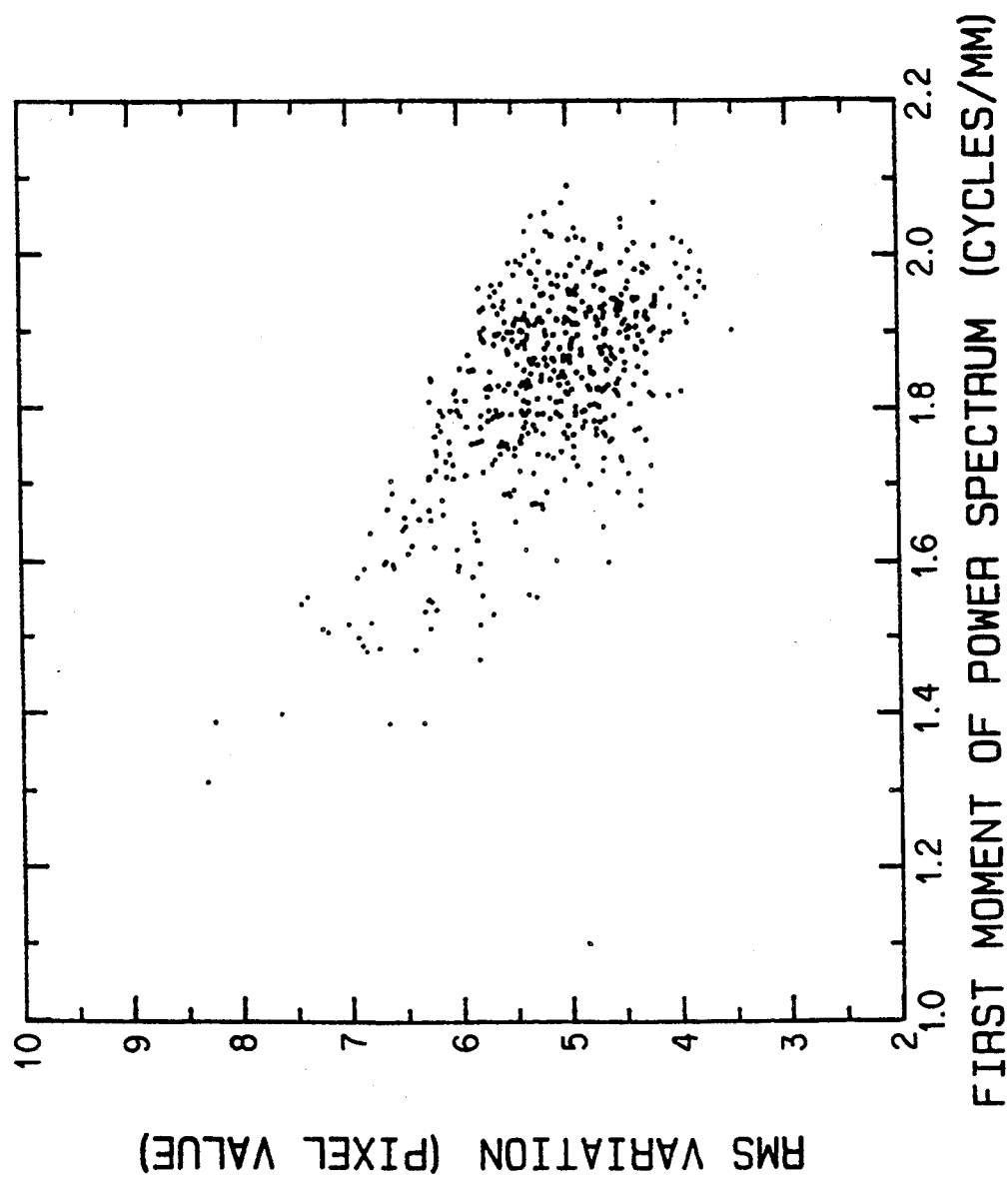
FIG. 12 shows the texture measures of the ROIs initially selected from the peripheral lung regions.
Figure 13:
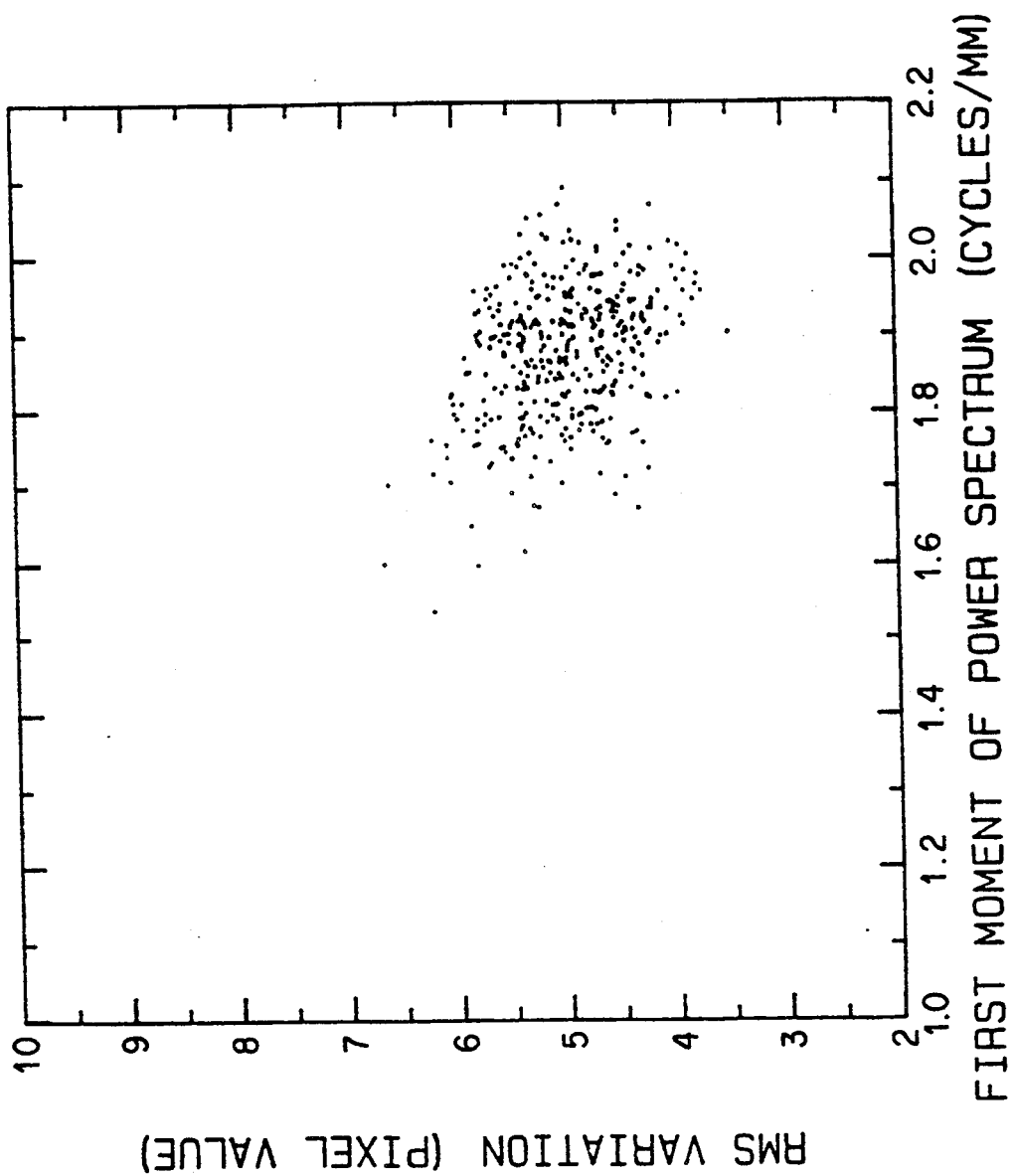
FIG. 13 shows texture measures of the ROIs automatically selected after removal of 30% of the initially selected ROIs which contain sharp edges.

FIGS. 12 and 13, respectively, illustrate the texture measures of the ROIs initially selected from the peripheral lung regions and the texture measures of the ROIs automatically selected by removal of 30% of the initially selected ROIs containing sharp edges. FIG. 13 indicates that a number of the ROIs having sharp edges which were removed in the 30% sample came from the central region data points of FIG. 12. In other words, these data points had high R values and lower M values as would be expected from high gradient sharp edged ROIs. It is important to note that many texture measures which look "abnormal" can be eliminated by this method.

Figure 14:
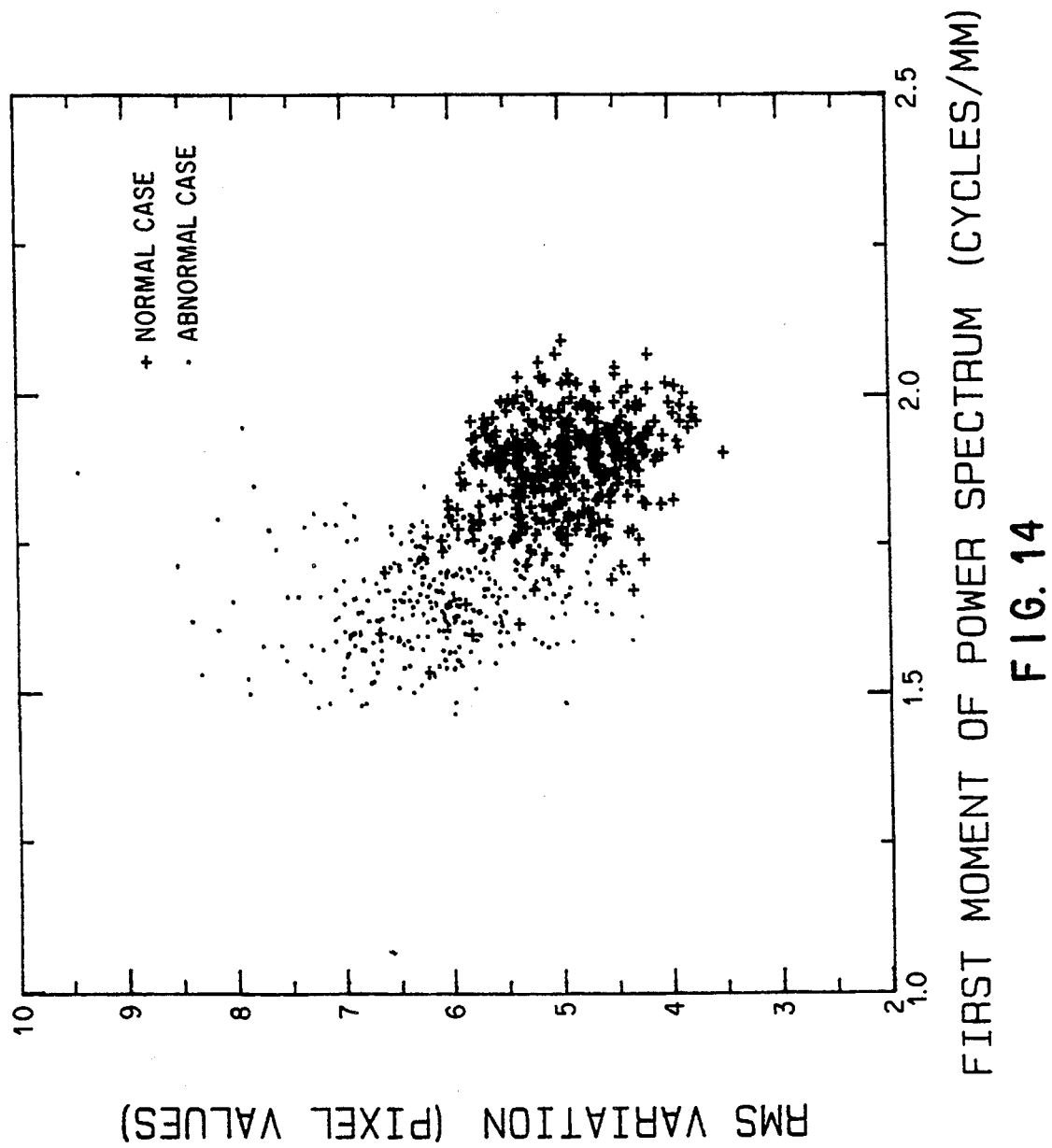
FIG. 14 illustrates the texture measures of the ROIs automatically selected, for both abnormal and normal chest images.

FIG. 14 shows texture measures for both normal and abnormal images, after 30% of initially selected ROIs have been removed. The RMS variation, R, values are plotted along the vertical axis and the first moment of power spectrum, P, values are plotted along the horizontal axis. A majority of the ROIs which represent a normal lung are located in a region below and to the right of the abnormal case data points, and are indicated by the "+" signs.

All of these results appear to indicate that the standard deviation of the gradient-weighted edge orientation histogram is a useful measure for removing the ROIs with sharp edges. A 30% fraction for removal of the ROIs with sharp edges was used. This fraction was selected by considering the tradeoff between the maintenance of meaningful ROIs with normal (and abnormal) lung textures and the removal of unwanted ROIs with sharp edges. Approximately 200–400 ROIs remained for lung texture analysis in each chest image even after removing 30% of the initially selected ROIs; this is more than 20 times the number of ROIs used in the prior art method disclosed in U.S. Pat. No. 4,839,807.

Figure 15A:
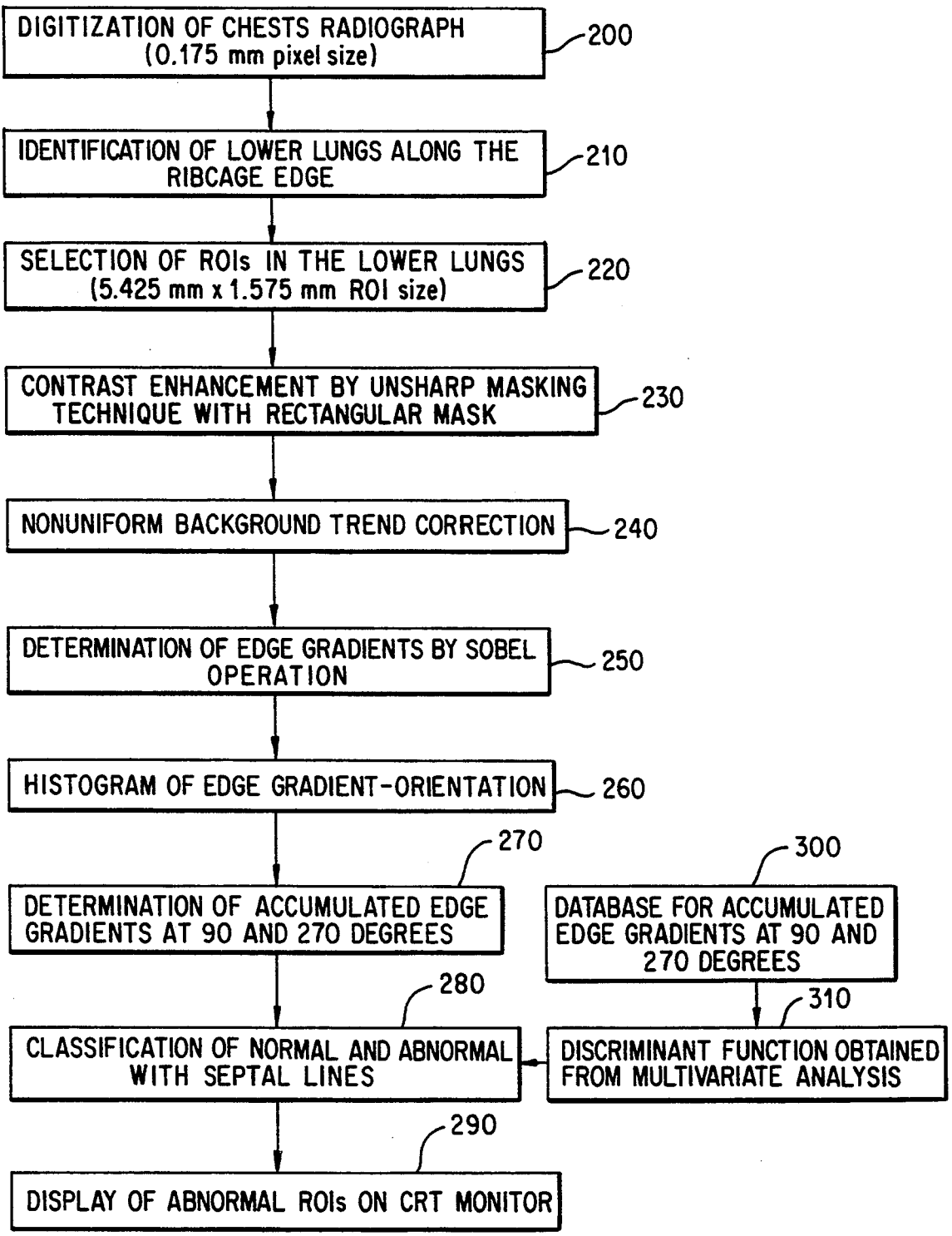
FIG. 15A is a flowchart illustrating the overall scheme for automated detection of septal lines in digital chest radiographs and the classification of normal ROIs and abnormal ROIs having septal lines.

The overall scheme for the detection of septal lines is shown in FIG. 15A. First, a conventional chest radiograph is digitized (block 200), with a laser scanner at a pixel size of 0.175 mm and 1024 gray levels (10-bit quantization). In the next step, (block 210) the lower lung regions to be analyzed are identified, as will be described in detail later.

Because septal lines are commonly recognized in the outer areas of the lower lung fields, the regions to be analyzed by computer are selected automatically in narrow areas along the rib cage edges in both lower lung areas (block 220). Therefore, many rectangular regions of interest (ROIs) with 31×9 pixels (5.425 mm×1.575 mm) are determined continuously in these lower lung areas. Approximately 300 ROIs are obtained for a given chest image. In order to enhance the local contrast of septal lines, which are represented by subtle horizontal lines, the chest image is processed by using a conventional unsharp masking filter with a rectangular mask (block 230). For a detailed discussion of the unsharp masking technique used, reference can be made to Pratt, "Digital Image Processing", John Wiley & Sons, New York (1978), McMahon et al, "The effect of Digital Unsharp Masking on the Detectability of Inerstitial Infiltrates and Pneumothoraces", Proc. SPIE, Vol. 555, pp. 246–252 (1985), Ishida et al, "High Quality Digital Radiographic Images: Improved detection of Low Contrast Objects and Preliminary Clinical Studies," *Radiographics*, Vol. 13, pp. 325–328 (1983)

The nonuniform background trend in each ROI is then corrected by means of a surface-fitting technique (block 240). Next, a gradient-weighted edge orientation histogram is calculated (block 260), after a Sobel operator is used on all pixels included in each ROI (block 250), so that the unique angular components associated with septal lines can be identified.

The detection of a septal line in each ROI is made with a mathematical linear discriminant function. Such functions are widely used in the field of statistics and generally involve comparisons of measured parameter values with other known, predetermined parameters and then analyzing these values in order to identify (or classify) data. In the present invention, this multivariate analysis technique of using a linear discriminant function is based on accumulated edge gradients at two orientations (90 and 270 degrees) in the gradient-orientation histogram (block 270). The linear discriminant function has been determined by multivariate analysis on a predetermined database (block 330), which database (block 300) includes 36 chest images, some with normal and some with abnormal lungs. The individual ROIs are then classified as either normal or abnormal based on the determination of accumulated edge gradients at 90 and 270 degrees for candidate septal lines and comparison of their values with values stored in a database (block 280). Finally, all ROIs with detected septal lines are displayed on a CRT monitor (block 290) by means of markers superimposed on the chest image.

For identification of lower lung areas along the rib cage edge, the techniques described in U.S. Pat. No. 4,851,984 are employed, in which both the rib cage boundary and the diaphragm boundary are determined. Rib cage edges in the lower lungs are first determined from the minimum value of the second derivatives of horizontal signatures. Detected edge points are fitted by a polynomial curve for smoothing of the data points. Diaphragm edges are determined by the maximum value in the first derivatives of vertical signatures and then smoothed by the curve-fitting technique with the polynomial function. Therefore, the costphrenic sulcus is determined as a crossing point of the two smoothed curves for the rib cage boundary and the diaphragm boundary.

FIG. 15B illustrates the overall scheme for the system used for the implementation of automated septal lines detection. An X-ray image is digitized and input into digital input device 120 and then stored in memory 121. This image is then simultaneously output to a ribcage detector 122 and a diaphragm edge detector 123, and also to display 134. The lower peripheral lung areas are identified by selector 124 and this boundary information is output to ROIs selector 126 which also receives input from grid pattern generator 125. An unsharp masking filter 127 is applied in order to enhance the digital image by increasing the sensitivity, and then a background trend correction means 129 is used to further correct for normal background structures appearing in the ROIs. A well known two-dimensional surface generator 128 is employed to create the trend corrected image.

Next, edge gradient calculator 130 generates edge gradient values which are used by histogram generator 131 to perform a graphical analysis to be output to an accumulated edge gradient comparator 133 which compares standard deviation edge gradient values with predetermined threshold values stored in database memory 132. The ROI which contains a septal line is then discriminated as being either normal or abnormal by classifier means 136. Symbols generator 135 outputs various symbols indicative of the size and severity of the septal lines. These symbols are then superimposed on the original digital image in display device 134.

Figure 16:
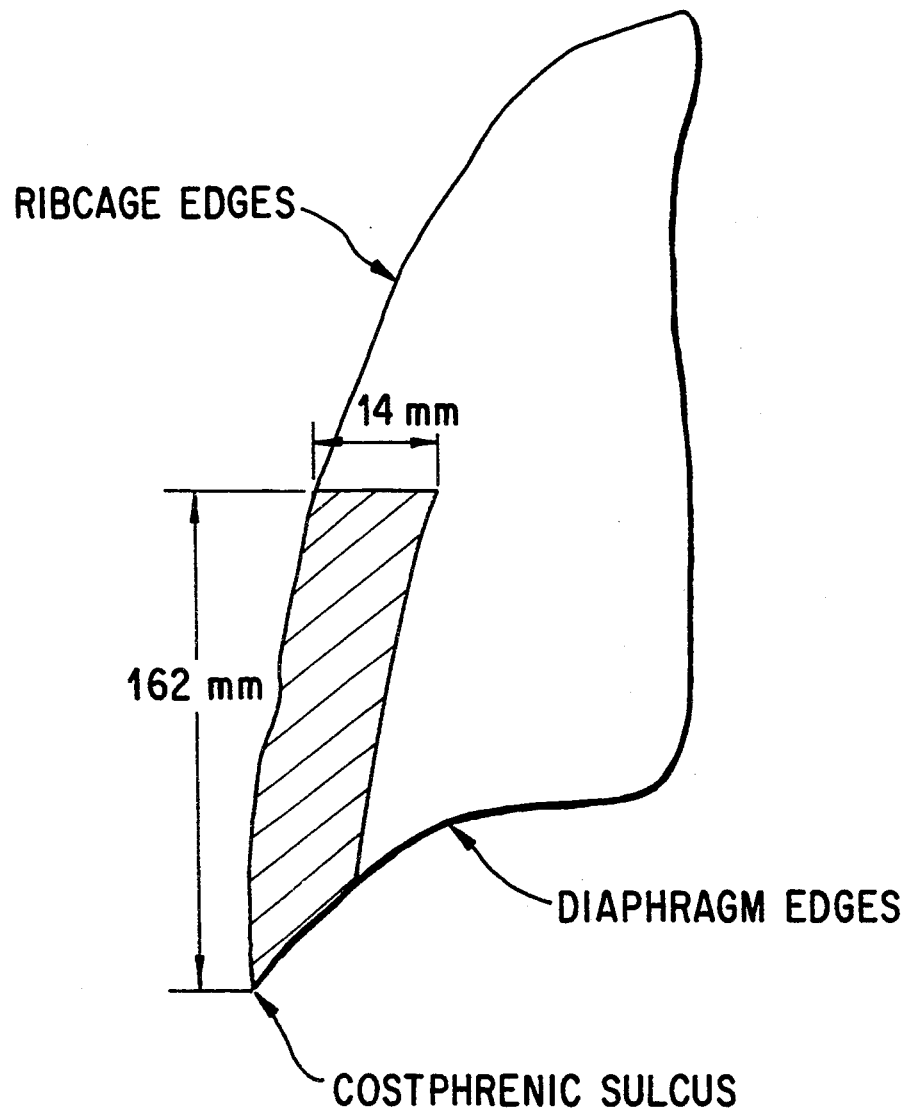
FIG. 16 is an illustration of the method for selecting the outer boundaries of the lower lung region to be analyzed for the presence of septal lines.

As illustrated in FIG. 16, the region to be examined for septal lines is determined in each lung by the area surrounded by (1) the outer boundary which equals the smoothed rib cage boundary, (2) the inner boundary which is the outer boundary curve parallel-shifted into the lung field by a distance of approximately 14 mm, (3) the lower boundary which equals the smoothed diaphragm curve, and (4) the upper boundary which is a horizontal line at a distance of approximately 162 mm above the costphrenic sulcus. These boundaries were determined empirically.

Because septal lines in chest images are represented by thin, long linear opacities in the horizontal direction, the detection of septal lines based on gradient-orientation histogram analysis can be affected by the size and shape of the ROI. Therefore, the effect of the side length of the ROI was investigated, by changing the vertical size of the ROI from 0.875 mm to 3.675 mm and also the horizontal size of the ROI from 1.925 mm to 8.925 mm, on the detectability of septal lines by using receiver operating characteristic (ROC) curves. The results indicated that a rectangular ROI with a long side length in the horizontal direction was effective in improving the detectability of septal lines. An ROI of 5.425 mm (horizontal size)×1.575 mm (vertical size) was therefore selected for analysis.

In order to enhance the image contrast of patterns including subtle density variations in the vertical direction, and thus to increase the contrast of septal lines which run in the horizontal direction, the chest images were processed by using the unsharp mask filtering (UMF) technique with a rectangular mask. The size of the mask was 0.875 mm×2.275 mm, and the weighting factor was 3.0.

The density distribution of the lung field in chest radiographs includes both fine fluctuating texture patterns related to septal lines and a gradual change due to the gross anatomy of the lung and chest wall. Therefore, in order to detect septal lines with high sensitivity, the nonuniform background trend must be removed. A surface-fitting technique using the 4th-order polynomial function to estimate the background trend in each ROI was employed. The estimated background trend was subtracted from the original image, yielding a background trend-corrected image which was subjected to subsequent computer analysis. The background trend correction technique used in a preferred embodiment is described in U.S. Pat. No. 4,851,984.

Because septal lines contain very narrow patterns of very low contrast, it is generally difficult to detect them visually, even if linear horizontal patterns in chest images are enhanced. Therefore, the distribution of edge gradients within a relatively small ROI have been carefully examined. This approach is based on gradient-orientation histogram analysis.

Figure 17:
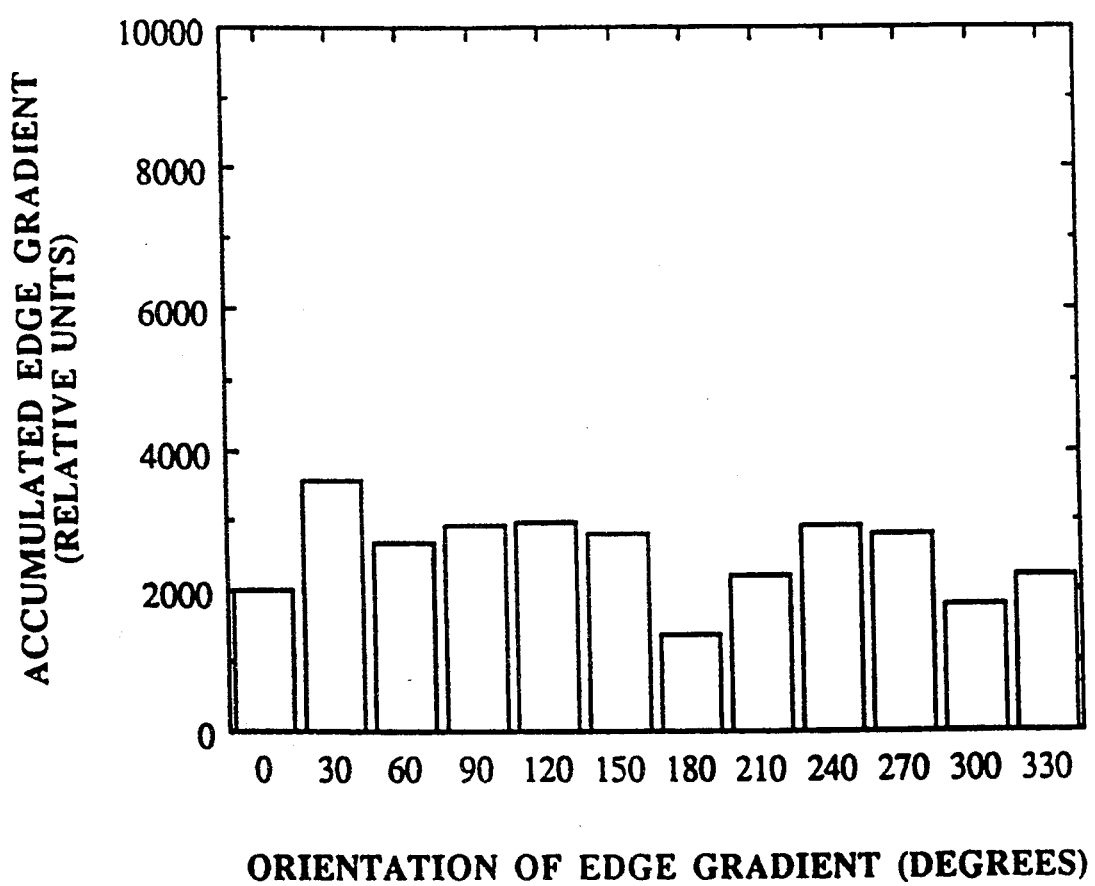
FIG. 17 illustrates a gradient-orientation histogram showing the pattern obtained for a normal ROI without the presence of septal lines.
Figure 18:
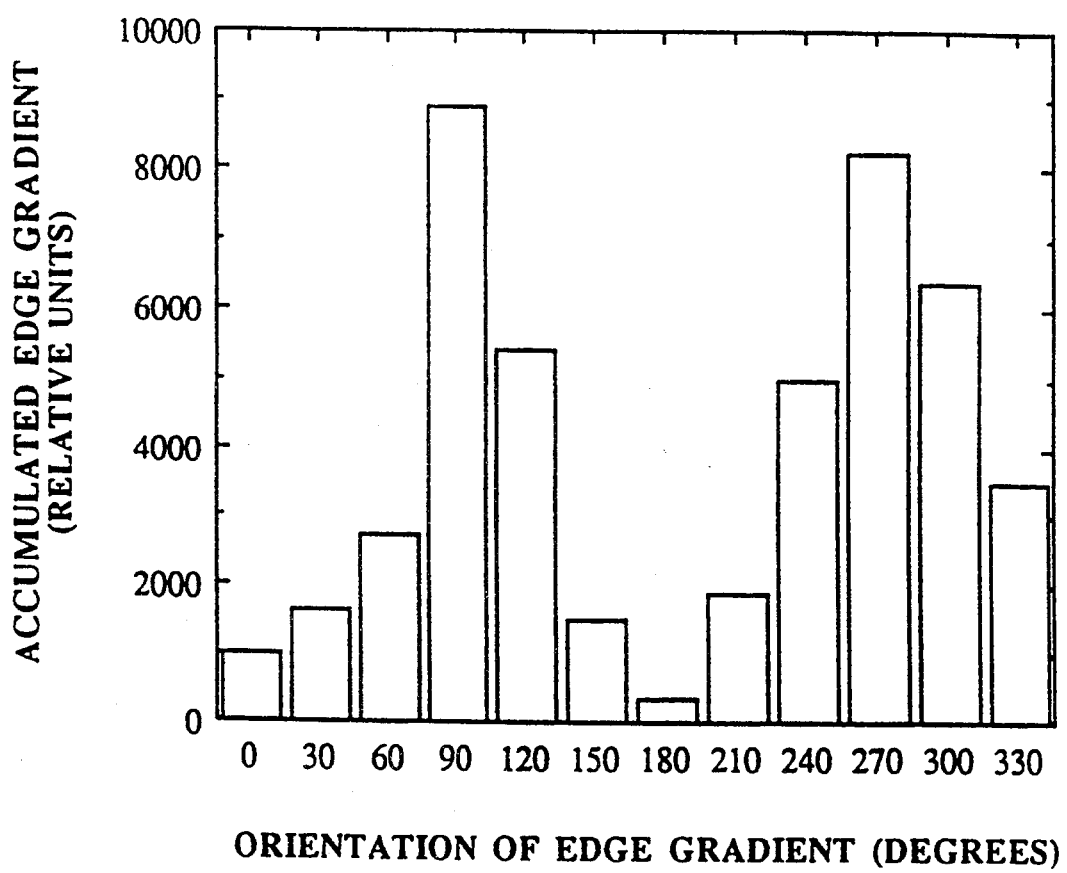
FIG. 18 illustrates a gradient-orientation histogram showing the pattern obtained for an abnormal ROI with septal lines.

The gradient-orientation histograms obtained for two ROIs, one without and the other with septal lines, are shown in FIGS. 17 and 18. For the ROI without septal lines, the distribution of accumulated edge gradients is relatively uniform and the average value is relatively small. However, for the ROI with septal lines, the accumulated edge gradients become very large at two angles, near 90 and 270 degrees. It has been found that this is a unique feature of the ROI which includes septal lines, namely, the gradient-orientation histogram has two large peaks at G(90) and G(270).

Figure 19:
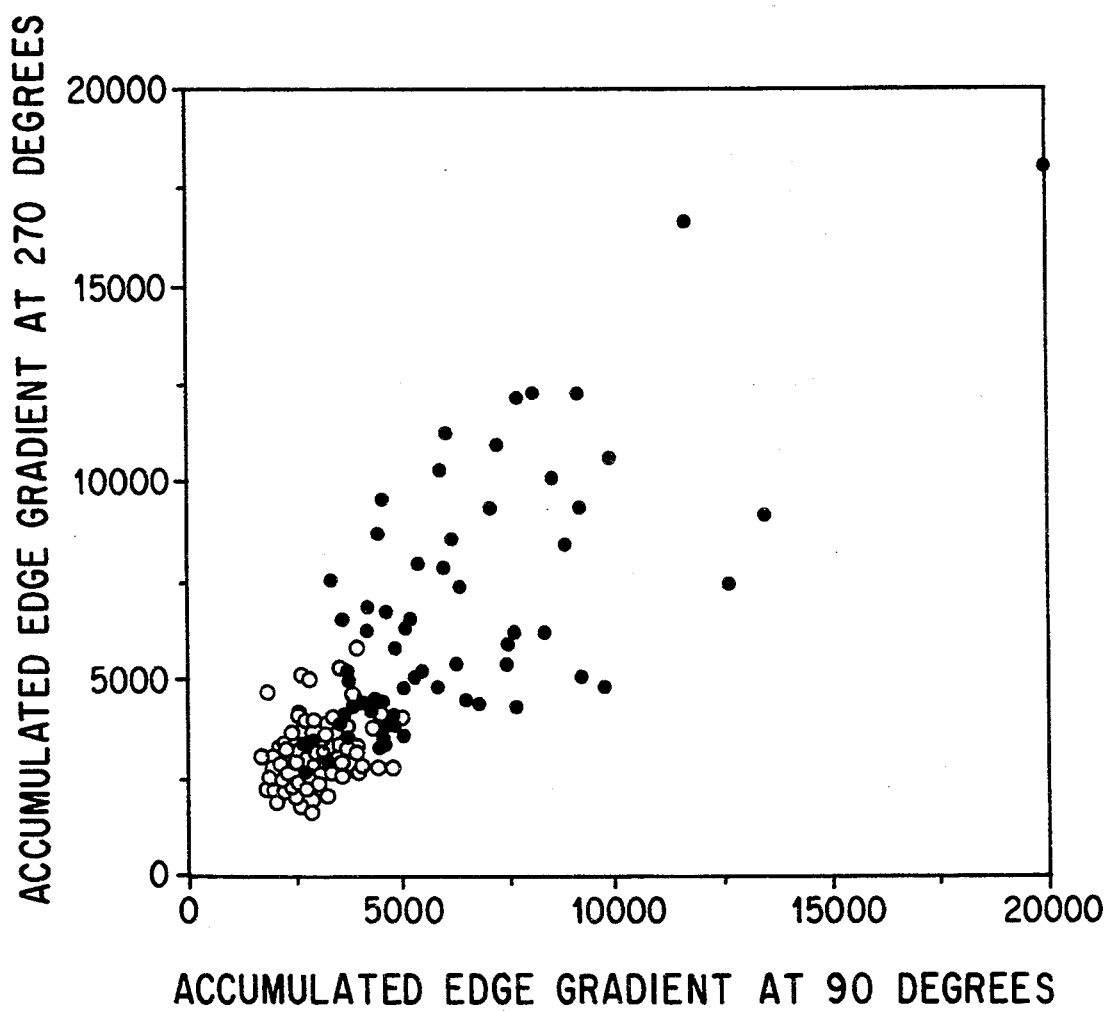
FIG. 19 shows the distributions of accumulated edge gradients at 90° and 270° obtained from a database of chest images that included 100 normal ROIs without septal lines and 63 abnormal ROIs with septal lines.

FIG. 19 shows the distributions of accumulated edge gradients at 90 and 270 degrees obtained from a database of chest images that included 100 normal ROIs without septal lines as shown by open circles and 63 abnormal ROIs with septal lines as indicated by the filled in circles. It is apparent that the accumulated edge gradients for abnormal ROIs at 90 and 270 degrees are generally greater than those for normal ROIS. However, since there are some correlations between the accumulated edge gradients at 90 and those at 270 degrees, it is expected that a linear discriminant function derived from multivariate analysis using the two accumulated edge gradients at 90 and 270 degrees can distinguish between normal and abnormal ROIs better than can the accumulated edge gradients at either 90 degrees or 270 degrees alone.

Figure 20:
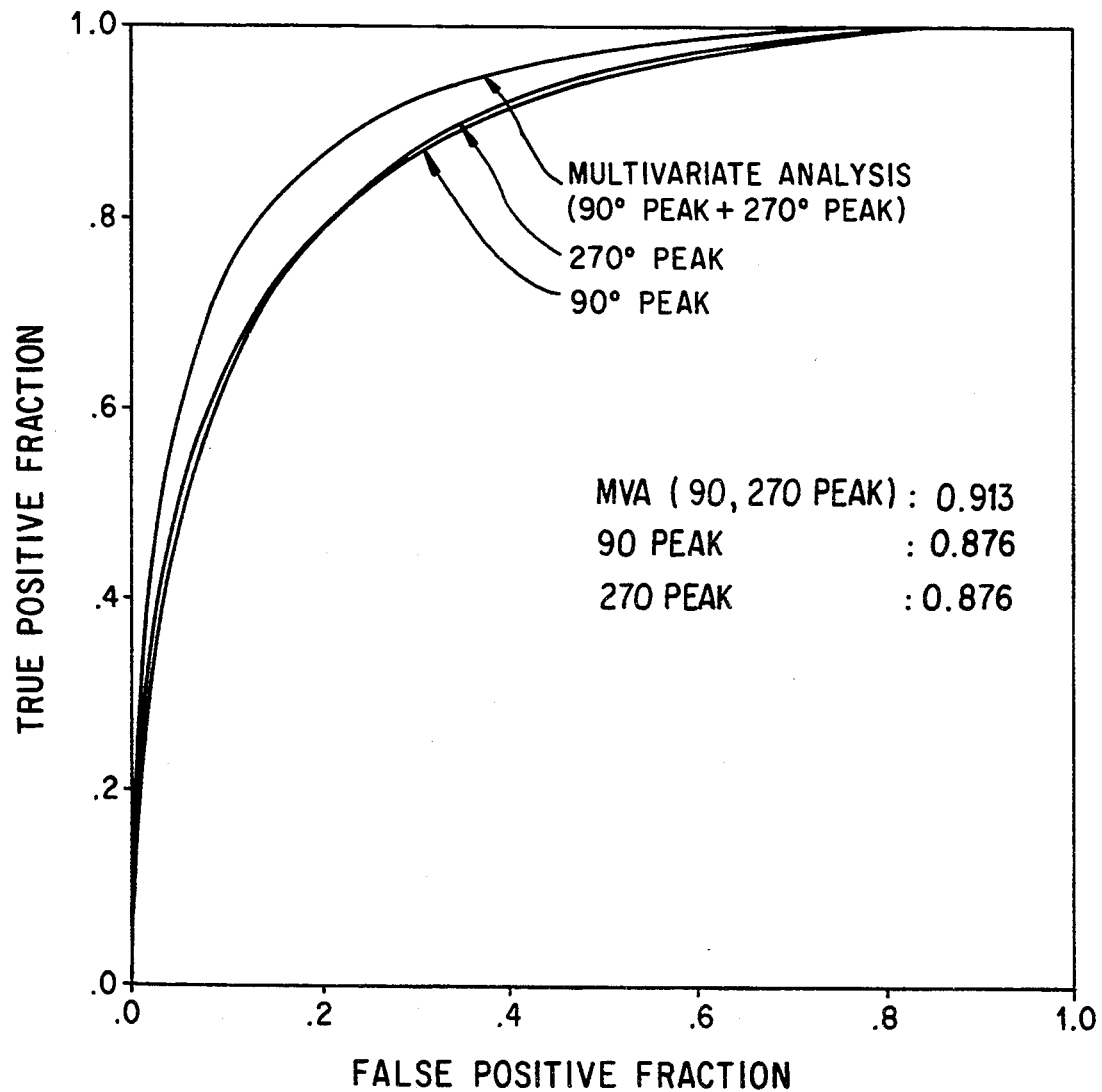
FIG. 20 shows a comparison of three ROC curves obtained for 18 normal and 18 abnormal chest images which included a total of 121 septal lines, for the classification between normal and abnormal ROIs.

FIG. 20 shows a comparison of three ROC curves obtained for 18 normal and 18 abnormal chest images which included a total of 121 septal lines, for the classification between normal and abnormal ROIs based on three different criteria, namely, G(90) alone, G(270) alone, and the combination of G(90) and G(270) with use of the discriminant function. The ROC curve indicates the relationship between the true-positive fraction (corresponding to correct detection of septal lines in abnormal ROIs) and the false-positive fraction (corresponding to incorrect detection of septal lines in normal ROIs) as a function of a threshold level. For the ROC curve obtained with G(90) alone, the accumulated edge gradient at 90 degrees is used as a threshold criterion. For the distinction between normal and abnormal ROIs, the ROIs that contain an accumulated edge gradient greater than a given threshold level are classified as positive ROIs.

Next, the true-positive fraction is determined from the number of positive ROIs correctly classified, divided by the total number of actually positive ROIs. It is apparent from FIG. 20 that the accumulated edge gradient at either 90 or 270 degrees can distinguish well between normal ROIs and abnormal ROIs with septal lines. However, it should be noted that the detection accuracy of septal lines in chest images is improved considerably by the use of multivariate analysis with the discriminant function, as compared with the accumulated edge gradient at either 90 or 270 degrees alone.

Figure 21:
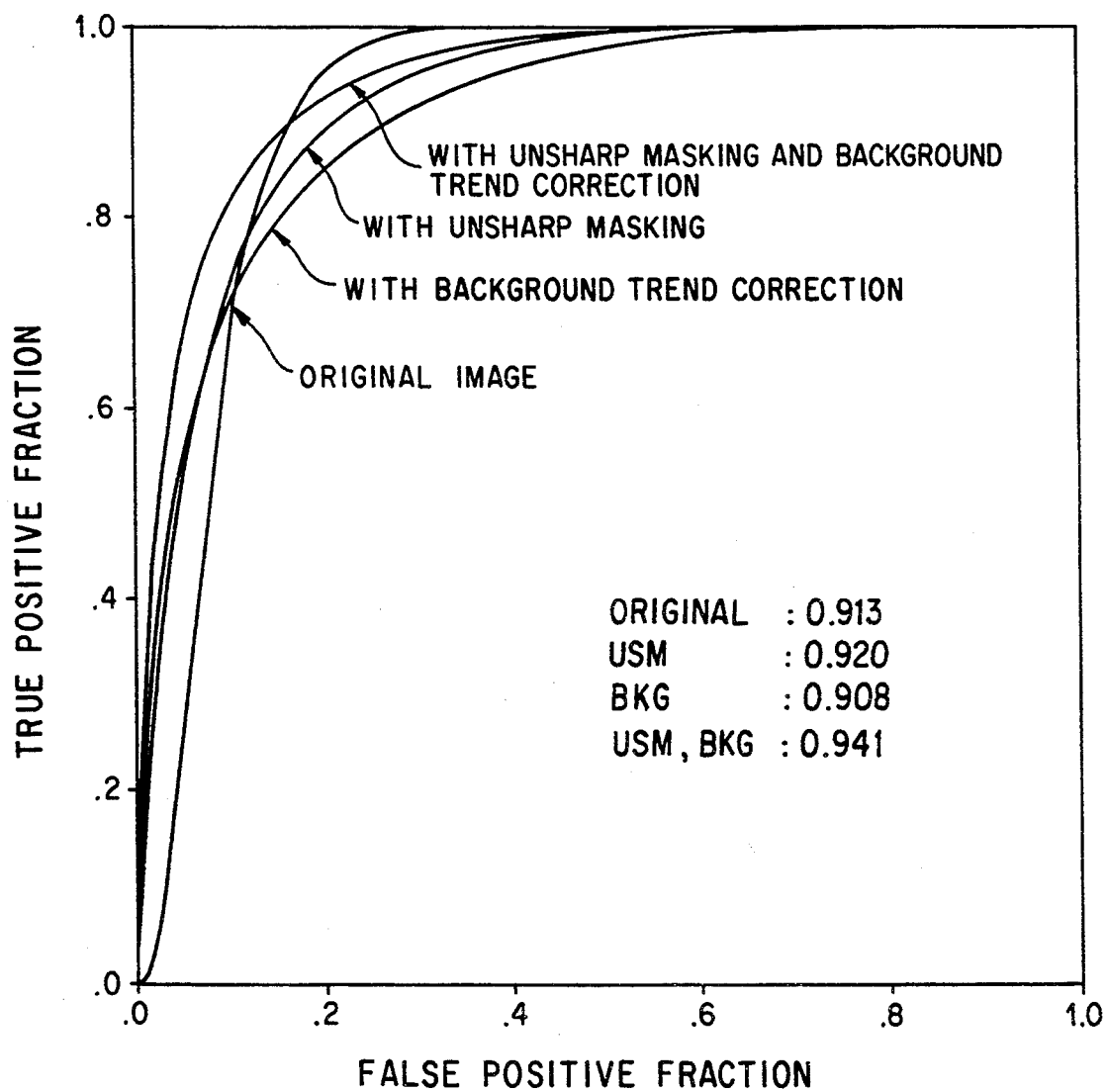
FIG. 21 shows a comparison of ROC curves obtained with various types of image processing applied to chest images, in order to determine the effects of image processing on the classification between normal lungs and abnormal lungs.

FIG. 21 shows a comparison of ROC curves obtained with various types of image processing applied to chest images, in an effort to determine the effect of image processing on the classification between normal lungs and abnormal lungs. An abnormal lung is defined as one containing more than eight abnormal ROIs based on gradient-orientation histogram analysis. This criterion was determined empirically. The results shown in FIG. 21 indicate that the use of background trend corrections and unsharp masking can improve the performance of the computerized scheme for classifying normal lungs and lungs with septal lines.

Fully automated methods for ROI selection in lung texture analysis and for the detection of septal lines have been developed. The edge gradient analysis based on the gradient-weighted edge orientation histogram is very effective for identification and removal of the ROIs with sharp edges. Approximately 20 times more ROIs as compared with the previous technique can be selected for the lung texture analysis. The RMS variation and the first moment of the power spectrum for abnormal lungs with various interstitial diseases show significant differences from those for normal lungs. The computerized scheme for lung texture analysis and the detection of septal lines using an automated selection of ROIs can be implemented in the near future as an aid to radiologists for more objective and accurate interpretation of chest images in clinical situations.

The method and system of the present invention is not to be construed as being limited to the analysis of lungs, but rather the computerized scheme disclosed herein can be used in the analysis of normal and abnormal patterns included in such other medical applications as magnetic resonance imaging techniques (MRI), CT scans, ultrasound images, bone radiography, mammography, etc.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A computer implemented method for automated detection of abnormalities in digital chest radiographs comprising:
   identifying peripheral lung areas of a digital chest radiograph, stored in an image memory in a computer, to be analyzed;
   preselecting, using said computer, a sample of numerous contiguous regions of interest (ROIs) included in said peripheral lung areas;
   performing a background trend correction, using said computer, on each of the ROIs of said preselected sample so as to produce corrected image data;
   performing an edge gradient analysis, using said computer, on each of the ROIs of said preselected sample in order to distinguish sharp-edged ROIs from ROIs with sharp edges;
   removing a portion of said sharp-edged ROIs from said preselected sample; and
   performing texture measurements on the remaining ROIs of said preselected sample which have not been removed in said removing step.

2. The method according to claim 1, wherein said step of preselecting a sample of numerous contiguous ROIs comprises:
   selecting numerous square ROIs, each having a matrix size which is small enough to fit between a pair of adjacent ribs, wherein said ROIs are selected so as to be located within the peripheral lung areas in order to form a grid of adjacent square ROIs covering nearly the entire peripheral lung areas.

3. The method according to claim 1, wherein said step of preselecting a sample of numerous contiguous ROIs comprises:
   initially selecting approximately 400 to 600 ROIs so as to form a grid of adjacent square ROIs covering nearly the entire peripheral lung areas.

4. The method according to claim 1, wherein said step of identifying peripheral lung areas comprises:
   selecting an upper boundary of a peripheral lung area at a distance below the lung apex, said distance equal to approximately 20% of the lung height;

selecting a lower boundary of said peripheral lung area to be the top of the diaphragm;

selecting an outer boundary of said peripheral lung at a location approximately 96% of the distance from a midline location of said chest radiograph to an edge of the rib cage; and selecting an inner boundary which changes linearly from 50% of the distance from said midline of the chest radiograph image to the rib cage edge up to 80% at the lower boundary.

5. The method according to claim 1, wherein said step of performing an edge gradient analysis comprises:

detecting edge gradients using a gradient-weighted edge orientation histogram for detecting step edges or line edges in each of the ROIs of said preselected sample.

6. The method according to claim 5, comprising:

calculating a standard deviation of said gradient-weighted edge orientation histogram for use as a measurement in determining the sharp-edged ROIs to be removed.

7. The method according to claim 6, wherein said step of removing comprises:

eliminating those ROIs exhibiting high edge gradients having standard deviations in a selected upper percentage of standard deviations calculated for edge gradients of each ROI from said preselected sample.

8. The method according to claim 6, wherein said step of removing comprises:

eliminating said sharp-edged ROIs with edge gradient standard deviation values above a predetermined threshold value.

9. The method according to claim 1, wherein said step for performing texture measurements comprises:

determining the RMS variation, R, and the first moment of the power spectrum, M, where R represents the magnitude of the texture of an ROI and M represents the coarseness or fineness of the texture.

10. The method according to claim 1, comprising:

manually selecting individual ROIs from a normal disease-free chest radiograph, wherein said manually selected ROIs are selected from three regions including rib edges, areas over ribs and intercostal areas, in order to obtain predetermined texture measurements and edge gradient analyses of said ROIs from said three regions in order to provide information about ROIs with known locations.

11. The method according to claim 1, comprising:

displaying said texture measurements superimposed on a chest image utilizing various sizes and shapes of markers representing the type and severity of lung textures of said ROIs.

12. A computer system for automated detection of abnormalities in digital chest radiographs, comprising:

means for identifying peripheral lung areas of a digital chest radiograph to be analyzed;

means for preselecting a sample of numerous contiguous regions of interest (ROIs) included in said peripheral lung areas;

means for performing a background trend correction on each of the ROIs of said preselected sample so as to produce corrected image data;

means for performing an edge gradient analysis on each of the ROIs of said preselected sample in order to distinguish sharp-edged ROIs from ROIs without sharp edges;

means for removing a portion of said sharp-edged ROIs from said preselected sample; and means for performing texture measurements on the remaining ROIs of said preselected sample which have not been removed in said removing step.

13. The system according to claim 12, wherein said means for preselecting a sample of numerous contiguous ROIs comprises:

means for selecting numerous square ROIs having a matrix size small enough to fit between a pair or adjacent ribs, wherein said ROIs are selected so as to be located within the peripheral lung areas in order to form a grid of adjacent square ROIs covering nearly the entire peripheral lung areas.

14. The system according to claim 12, wherein said means for preselecting a sample of numerous contiguous ROIs comprises:

means for initially selecting approximately 400 to 600 ROIs so as to form a grid of adjacent square ROIs covering nearly the entire peripheral lung areas.

15. The system according to claim 12, wherein said means for identifying peripheral lung areas comprises:

means for selecting an upper boundary of a peripheral lung area at a distance below the lung apex, said distance equal to approximately 20% of the lung height;

means for selecting a lower boundary of said peripheral lung area to be the top of the diaphragm;

means for selecting an outer boundary of said peripheral lung area at a location approximately 96% of the distance from a midline of said chest radiograph to an edge of the rib cage; and means for selecting an inner boundary which changes linearly from 50% of the distance from the midline of said chest radiograph image to the rib cage edge up to 80% at the lower boundary.

16. The system according to claim 12, wherein said means for performing an edge gradient analysis further comprises:

means for detecting edge gradients using a gradient-weighted edge orientation histogram for detecting step edges or line edges in each of the ROIs of said preselected sample.

17. The system according to claim 16, further comprising:

means for calculating a standard deviation of said gradient-weighted edge orientation histogram for use as a measurement in determining the sharp-edged ROIs to be removed.

18. The system according to claim 17, wherein said means for removing comprises:

means for eliminating those ROIs which exhibit high edge gradients having standard deviations in a selected upper percentage of all calculated standard deviations.

19. The system according to claim 17, wherein said means for removing comprises:

means for eliminating said sharp-edged ROIs with standard deviation values above a predetermined threshold value.

20. The system according to claim 12, wherein said means for performing texture measurements comprises:

means for determining the RMS variation, R, and the first moment of the power spectrum, M, where R represents the magnitude of the texture of an ROI and M represents the coarseness or fineness of the texture.

21. The system according to claim 12, comprising:

means for manually selecting individual ROIs from a normal disease-free chest radiograph, wherein said means for manually selecting ROIs selects said ROIs from three regions including rib edge regions, areas over ribs and intercostal areas, in order to obtain predetermined texture measurements and edge gradient analyses of said ROIs from said three regions to provide a database of information about ROIs with known locations.

22. The system according to claim 12, further comprising:
means for displaying said texture measurements superimposed on a chest image utilizing various sizes and shapes of markers representing the type and severity of lung textures of said ROIs.

23. A computer implemented method for automated detection of septal lines in a digital chest radiograph, stored in an image memory in a computer, comprising:
identifying a lower lung area along rib cage edges in said digital chest radiograph;
preselecting, using said computer, a sample of numerous contiguous regions of interest (ROIs) within said lower lung area;
performing contrast enhancement, in said computer, using an unsharp masking technique with a rectangular mask;
removing a background trend from each individual ROI;
calculating accumulated edge gradients for each of said individual ROIs;
generating an edge-gradient orientation histogram, in said computer, for each of said individual ROIs based on said calculated accumulated edge gradients;
comparing, using said computer, each generated edge-gradient orientation histogram with predetermined values stored in a database to obtain a comparison result for each of said individual ROIs;
determining if septal lines are present in each of said individual ROIs based on said comparison result for each of said individual ROIs; and
classifying, using said computer, each of said individual ROIs as normal or abnormal having septal lines.

24. The method according to claim 23, further comprising:
displaying of said abnormal ROIs on a CRT monitor screen.

25. The method according to claim 23, wherein said step of performing an edge gradient analysis comprises:
determining accumulated edge gradients at 90° and 270° and wherein said edge gradients are determined by use of a Sobel operation.

26. The method according to claim 23, wherein said step of identifying said lower lung area includes determining locations of rib cage and diaphragm boundaries.

27. The method according to claim 26, wherein said locations of rib cage boundaries are determined from minimum values of the second derivatives of horizontal signatures.

28. The method according to claim 26, wherein said locations of said diaphragm boundary are determined from maximum values of the first derivatives of vertical signatures which are then smoothed by a curve-fitting technique with a polynomial function.

29. The method according to claim 23, wherein said sample of ROIs include a plurality of rectangular ROIs comprising 31×9 pixels which are determined continuously in said lower lung area so as to form a grid of adjacent rectangular ROIs covering nearly the entire lower lung area.

30. The method according to claim 23, wherein said step of classifying said ROIs comprises:
classifying said ROIs as either normal or abnormal using a linear discriminant function which is determined by multivariate analysis of a database of known samples containing normal and abnormal ROIs.

31. The method according to claim 23, wherein said step of removing said background trend comprises using a surface-fitting technique with a 4th-order polynomial function.

32. The method according to claim 23, further comprising plotting ROC curves which indicate the relationship between a true positive fraction corresponding to correct detections of septal lines in abnormal ROIs, and false positive fraction corresponding to incorrect detection of septal lines in normal ROIs as a function of a threshold level.

33. A computer system for automated detection of septal lines in digital chest radiographs, comprising:
means for identifying a lower lung area along rib cage edges;
means for preselecting a sample of numerous contiguous regions of interest (ROIs) within said lower lung area;
means for performing contrast enhancement using an unsharp masking technique with a rectangular mask;
means for removing a background trend from each individual ROI;
means for calculating accumulated edge gradients for each of said individual ROIs;
means for generating an edge-gradient orientation histogram for each individual ROI based on said calculated accumulated edge gradients;
means for comparing each generated edge-gradient orientation histogram with predetermined values stored in a database to obtain a comparison result for each individual ROI;
means for determining if septal lines are present in each of said individual ROIs based on said comparison result for each of said individual ROIs; and
means for classifying each of said individual ROIs as normal or as abnormal having septal lines.

34. The system according to claim 33, further comprising:
CRT monitor means for displaying abnormal ROIs.

35. The system according to claim 33, wherein said means for performing an edge gradient analysis comprises:
means for determining accumulated edge gradients at 90° and 270° and wherein said edge gradients are determined by use of a Sobel operation.

36. The system according to claim 33, wherein said means for identifying said lower lung areas includes means for determining locations of rib cage and diaphragm boundaries.

37. The system according to claim 36, further comprising means for determining said locations of rib cage boundaries using minimum values of the second derivatives of horizontal signatures.

38. The system according to claim 36, wherein said locations of said diaphragm boundaries are determined from maximum values of the first derivatives of vertical signatures which are then smoothed by a curve-fitting technique with a polynomial function.

39. The system according to claim 33, wherein said sample of ROIs includes a plurality of rectangular ROIs comprising 31×9 pixels which are determined continuously in said lower lung area so as to form a grid of adjacent rectangular ROIs covering nearly the entire lower lung area.

40. The system according to claim 33, wherein said means for classifying said ROIs comprises:

means for classifying said ROIs as either normal or abnormal using a linear discriminant function which is determined by multivariate analysis of a database of known samples containing normal and abnormal ROIs.

41. The system according to claim 33, wherein said means for removing said background trend comprises a means for performing a surface-fitting technique with a 4th-order polynomial function.

42. The system according to claim 33, further comprising a means for plotting ROC curves which indicate the relationship between a true positive fraction corresponding to correct detection of septal lines in abnormal ROIs and false positive fraction corresponding to incorrect detection of septal lines in normal ROIs as a function of a threshold level.

* * * * *

UNITED STATES PATENT AND TRADEMARK OFFICE
CERTIFICATE OF CORRECTION

PATENT NO. : 5,343,390
DATED : August 30, 1994
INVENTOR(S) : Kunio Doi et al.

It is certified that error appears in the above-identified patent and that said Letters Patent is hereby corrected as shown below:

Column 16,
Line 43, change "with" to -- without --.

Signed and Sealed this

Nineteenth Day of November, 2002

Attest:

JAMES E. ROGAN
*Attesting Officer*   *Director of the United States Patent and Trademark Office*